United States Patent
Robertson et al.

(10) Patent No.: US 12,224,061 B2
(45) Date of Patent: Feb. 11, 2025

(54) DETERMINING LEVELS OF HYPERTENSION FROM RETINAL VASCULATURE IMAGES

(71) Applicant: OPTOS PLC, Dunfermline (GB)

(72) Inventors: Gavin Robertson, Dunfermline (GB); Alan Duncan Fleming, Dunfermline (GB)

(73) Assignee: OPTOS PLC, Dunfermline (GB)

(*) Notice: Subject to any disclaimer, the term of this patent is extended or adjusted under 35 U.S.C. 154(b) by 0 days.

(21) Appl. No.: 16/837,733

(22) Filed: Apr. 1, 2020

(65) Prior Publication Data
US 2020/0320693 A1  Oct. 8, 2020

(30) Foreign Application Priority Data
Apr. 4, 2019 (EP) .................. 19167391

(51) Int. Cl.
*G16H 50/20* (2018.01)
*G06T 5/40* (2006.01)
(Continued)

(52) U.S. Cl.
CPC ............ *G16H 50/20* (2018.01); *G06T 5/40* (2013.01); *G06T 7/0012* (2013.01); *G06T 7/11* (2017.01);
(Continued)

(58) Field of Classification Search
CPC ............ G06K 2209/05; G06K 9/0061; G06K 9/6267; G06T 2207/20081;
(Continued)

(56) References Cited

U.S. PATENT DOCUMENTS 5,125,730 A * 6/1992 Taylor ................ A61B 3/1241
351/221
6,996,260 B1 * 2/2006 Skands .................. A61B 3/12
382/128
(Continued)

FOREIGN PATENT DOCUMENTS

CN 105243669 A * 1/2016
CN 106943124 A   7/2017
(Continued)

OTHER PUBLICATIONS

S. Garg, J. Sivaswamy and S. Chandra, "Unsupervised curvature-based retinal vessel segmentation," 2007 4th IEEE International Symposium on Biomedical Imaging: From Nano to Macro, 2007, pp. 344-347, doi: 10.1109/ISBI.2007.356859. (Year: 2007).*
(Continued)

*Primary Examiner* — Gandhi Thirugnanam
(74) *Attorney, Agent, or Firm* — FAEGRE DRINKER BIDDLE & REATH

(57) ABSTRACT

A computer-implemented method, system, and computer-readable medium, for determining a level of hypertension of a person. Image data defining a retinal image of a retina of the person that has been captured by a retinal imaging system is acquired. Processing the image data is performed to identify a plurality of vessel segments present in the retinal image. Determining is performed of respective widths of vessel segments of at least a subset of the plurality of vessel segments present in the retinal image. Calculating, as a vascular summary metric, at least one average value or median value of the determined widths of the vessel segments present in the retinal image, is performed to determine a level of hypertension by which the person has been affected.

20 Claims, 9 Drawing Sheets

(51) Int. Cl.
- *G06T 7/00* (2017.01)
- *G06T 7/11* (2017.01)
- *G06T 7/155* (2017.01)
- *G06V 10/764* (2022.01)
- *G06V 10/82* (2022.01)
- *G06V 40/18* (2022.01)
- *G16H 30/40* (2018.01)
- *G16H 50/30* (2018.01)

(52) U.S. Cl.
CPC ............ *G06T 7/155* (2017.01); *G06V 10/764* (2022.01); *G06V 10/82* (2022.01); *G06V 40/193* (2022.01); *G16H 30/40* (2018.01); *G16H 50/30* (2018.01); *G06T 2207/20024* (2013.01); *G06T 2207/20036* (2013.01); *G06T 2207/20081* (2013.01); *G06T 2207/20084* (2013.01); *G06T 2207/30041* (2013.01)

(58) Field of Classification Search
CPC . G06T 2207/30041; G06T 2207/30101; G06T 7/11; G16H 50/20
See application file for complete search history.

(56) References Cited

U.S. PATENT DOCUMENTS

| | | | |
|---|---|---|---|
| 8,687,862 B2 | 4/2014 | Hsu et al. | |
| 8,787,638 B2* | 7/2014 | Zee | A61B 3/12 382/128 |
| 9,924,867 B2* | 3/2018 | Abramoff | A61B 3/0016 |
| 2010/0142767 A1* | 6/2010 | Fleming | G06T 7/11 382/117 |
| 2011/0026789 A1* | 2/2011 | Hsu | G06V 40/193 382/128 |
| 2012/0027275 A1* | 2/2012 | Fleming | G16H 50/20 382/128 |
| 2012/0195480 A1* | 8/2012 | González Penedo et al. | G06V 40/19 382/128 |
| 2012/0195481 A1* | 8/2012 | Gonzalez Penedo | G06T 7/0012 382/128 |
| 2012/0236259 A1* | 9/2012 | Abramoff | A61B 3/0016 351/246 |
| 2013/0114041 A1 | 5/2013 | Iftekharuddin et al. | |
| 2014/0294235 A1* | 10/2014 | Ishida | G06V 40/193 382/103 |
| 2014/0303013 A1* | 10/2014 | Hageman | A61K 31/4422 506/9 |
| 2016/0157737 A1 | 6/2016 | Huang et al. | |
| 2017/0100029 A1* | 4/2017 | Faber | G16H 50/50 |
| 2019/0014982 A1* | 1/2019 | Bhuiyan | G06V 10/267 |
| 2020/0242763 A1* | 7/2020 | Bhuiyan | G06T 7/73 |
| 2020/0320693 A1* | 10/2020 | Robertson | G06V 40/193 |

FOREIGN PATENT DOCUMENTS

| | | | | |
|---|---|---|---|---|
| EP | 3719808 A1 * | 10/2020 | | A61B 3/1241 |
| JP | H10-79034 A | 3/1998 | | |
| JP | 2006288842 A | 10/2006 | | |
| JP | 2008-22929 A | 2/2008 | | |
| JP | 2011-516200 A | 5/2011 | | |
| JP | 2014-504523 A | 2/2014 | | |
| JP | 2017-189292 A | 10/2017 | | |
| JP | 2017176210 A * | 10/2017 | | |
| JP | 2018-11726 A | 1/2018 | | |

OTHER PUBLICATIONS

Knudtson MD, Lee KE, Hubbard LD, Wong TY, Klein R, Klein BE. Revised formulas for summarizing retinal vessel diameters. Curr Eye Res. Sep. 2003;27(3):143-9. doi: 10.1076/ceyr.27.3.143.16049. PMID: 14562179. (Year: 2003).*

S. Manoj, Muralidharan, P. M. Sandeep, Neural Network Based Classifier for Retinal Blood Vessel Segmentation, Dec. 2013, International Journal of Recent Trends in Electrical & Electronics Engg, vol. 3, Issue 1, p. 44-53 (Year: 2013).*

Hubbard LD, Brothers RJ, King WN, Clegg LX, Klein R, Cooper LS, Sharrett AR, Davis MD, Cai J. Methods for evaluation of retinal microvascular abnormalities associated with hypertension/sclerosis in the Atherosclerosis Risk in Communities Study. Ophthalmology. Dec. 1999;106(12):2269-80. (Year: 1999).*

Tien Yin Wong; Ronald Klein; Barbara E. K. Klein; Stacy M. Meuer; Larry D. Hubbard, "Retinal Vessel Diameters and Their Associations with Age and Blood Pressure", Investigative Ophthalmology & Visual Science Nov. 2003, vol. 44, 4644-4650. (Year: 2003).*

Huiqi Li, W. Hsu, Mong Li Lee and Tien Yin Wong, "Automatic grading of retinal vessel caliber," in IEEE Transactions on Biomedical Engineering, vol. 52, No. 7, pp. 1352-1355, Jul. 2005 (Year: 2005).*

Modegi Toshio, Fundus image processing apparatus (English), JP-2017176210-A, Oct. 5, 2017, p. 1-16 (Year: 2017).*

Kawasaki R, Cheung N, Wang JJ, Klein R, Klein BE, Cotch MF, Sharrett AR, Shea S, Islam FA, Wong TY. Retinal vessel diameters and risk of hypertension: the Multiethnic Study of Atherosclerosis. J Hypertens. Dec. 2009;27(12):2386-93. doi: 10.1097/HJH. 0b013e3283310f7e. PMID: 19680136; PMCID: PMC2935621. (Year: 2009).*

Communication and European Search Report dated Oct. 9, 2019 relating to European patent application No. 19 167 391.2.

M.D. Knudtson et al., Revised formulas for summarizing retinal vessel diameters, Current Eye Research, vol. 27, No. 3, pp. 143-149. (2003).

E. Pellegrini et al., Blood vessel segmentation and width estimation in ultra-wide field scanning laser ophthalmoscopy, Biomedical Optics Express, vol. 5, No. 12, pp. 4329-4337 (2014).

Campbell et al., High Blood Pressure 2016: Why Prevention and Control Are Urgent and Important, The World Hypertension League, Int'l Soc. of Hypertension, World Stroke Organization, Int'l Diabetes Foundation, Int'l Council of Cardiovascular Prevention and Rehabilitation, Int'l Soc. of Nephrology, The Journal of Clinical Hypertension, vol. 18, No. 8, pp. 714-717, Aug. 2016.

Mordant et al., Spectral imaging of the retina, Cambridge Ophthalmological Symposium, Eye, 25, Macmillan Publishers Limited, pp. 309-320. Available from: http://www.nature.com/doifinder/10.1038/eye.(2010); 222.

Sangari et al., Convergence Analysis of Two Loss Functions in Soft-Max Regression, IEEE Transactions on Signal Processing, vol. 64, No. 5, pp. 1280-1288. (2016).

Cavinato et al., Spline-Based Refinement of Vessel Contours in Fundus Retinal Images for Width Estimation, 2013 IEEE 10th International Symposium on Biomedical Imaging: From Nano to Macro, pp. 872-875 (2013).

J. Aboshiha, Assessment of Accuracy and Precision of Quantification of Ultra-Widefield Images, Ophthalmology, vol. 122, No. 4, pp. 864-866, Apr. 2015.

G. Robertson et al., Screening for hypertension using retinal vascular calibre in ultra-widefield fundus imaging, Abstracts from the 2018 Annual Scientific Meeting of the British and Irish Hypertension Society (2018). (one sheet). (corresponding to Journal of Human Hypertension, vol. 32, No. 10, pp. 718-719).

Prospective Studies Collaboration, Age-specific relevance of usual blood pressure to vascular mortality: a meta-analysis of individual data for one million adults in 61 prospective studies, The Lancet 2002, vol. 360, pp. 1903-1913. (2002).

C. Agurto et al., Detection of Hypersensitive Retinopathy Using Vessel Measurements and Textural Features, by C. Agurto et al., 36th Annual International Conference of the IEEE Engineering in Medicine and Biology, pp. 5406-5409, (2014).

M. Niemeijer et al., Automatic determination of the artery-vein ratio in retinal images, Medical Imaging 2010: Computer-Aided Diagnosis, Proc. of SPIE vol. 7624, pp. 762401-1 to 762401-10 (2010).

D. Ortiz et al., System Development for Measuring the Arterious Venous Rate (AVR) for the Diagnosis of Hypertensive Retinopathy,

(56) References Cited

OTHER PUBLICATIONS

IEEE 2012 Andean Region International Conference 2012, pp. 53-56 (2012).
Notice of Reasons for Refusal issued in Japanese Patent Office Application No. 2020-068567 on Apr. 20, 2021 (Japanese Version with English Machine Translation attached).
Decision to Grant Patent issued in Japanese patent application 2020-068567 drafted Mar. 16, 2022 (1 sheet) (English translation attached).
A Comprehensive Study of Retinal Vessel Classification Methods in Fundus Images by Miri Maliheh et al., Journal of Medical Signals and Sensors, Jun. 30, 2017, XP55849915.
Automated retinal vessel type classification in color fundus images by H. Yu et al., Laser-based Micro- and Nanopackaging and Assembly II, vol. 8670, Feb. 26, 2013, p. 86700P, XP93086953.
European Search Report for EP Patent Application No. 19167391.2, Issued on Oct. 9, 2019, 9 pages.
Niemeijer et al., "Automated measurement of the arteriolar-to-venular width ratio in digital color fundus photographs", IEEE Trans Med Imaging, vol. 30, No. 11, Jun. 16, 2011, pp. 1941-1950.

* cited by examiner

DETERMINING LEVELS OF HYPERTENSION FROM RETINAL VASCULATURE IMAGES

This application claims the benefit of priority of European Patent Application No. 19 167 391.2, filed Apr. 4, 2019, the entire contents of which are incorporated by reference as if set forth fully herein.

FIELD

Example aspects herein generally relate to the field of image processing and, more particularly, to the processing of an image of a subject's retina to determine a level of hypertension by which the subject has been affected.

BACKGROUND

Hypertension is a common, generally asymptomatic condition that is a leading risk factor of death and disability world-wide. For example, around 30% of the adult population in the UK are thought to have hypertension (Campbell et al., "High blood pressure 2016: why prevention and control are urgent and important", International Society of Hypertension Executive: and Burrell, L., 2016, The Journal of Clinical Hypertension, 18(8), pp. 714-717) and approximately 30% of this group are to be estimated to be undiagnosed, leaving them at increased risk of cardiovascular disease and stroke. Typically, hypertension may be defined as a level of systolic blood pressure exceeding 140 mmHg. However, managing increased blood pressure in persons at moderate to high risk for hypertension may involve defining different levels of hypertension and/or lowering targets <140 mmHg (e.g. <130 mmHg or 120 mmHg) based on further emerging medical evidence.

Characteristics of retinal vessels are known to be associated with systemic disease such as diabetes and hypertension. The visibility of these vessels makes these a highly accessible source of health indicators or biomarkers for systemic disease. An image of the retina may be acquired by a fundus camera or scanning laser ophthalmoscope (SLO), for example, allowing a detailed view of the body's microcirculation to be obtained through non-invasive examination. Quantitative features derived from the retina, such as measurement of vascular calibre, i.e. thickness or diameter of the blood column, near the optic disc, have been associated with increased blood pressure and presence of hypertension. Typically, this association is characterised by a narrowing of the retinal arterioles, with little change to the venules. To mitigate for body size and eye magnification between subjects the artery-to-vein calibre ratio, commonly abbreviated AVR, is used as a surrogate for arteriolar calibre (Knudtson et al., "Revised formulas for summarizing retinal vessel diameters", 2003, Current Eye Research, 27(3), 143-149). Such a measure could translate into a test for undiagnosed hypertension using retinal imaging.

SUMMARY

The retinal vasculature is, however, highly variable and this makes the designation of a methodological approach for obtaining a metric for determining a level of hypertension from the retinal vascular very difficult.

For example, if it is decided to use a certain portion of the retina (a region of interest) in which to make a measurement of a vascular metric, then between individuals, there could be different numbers of vessel segments within this region. Also the distribution of branch points within the region, or between the region and the optic nerve head, will vary from one individual to another. Therefore, branching occurs an unknown (i.e. not visible) number of times between the central retinal artery and vein (within the optic nerve) and the arteries and the veins within the region of interest. These factors could influence the vascular width.

Known approaches to processing retinal images to detecting or predicting hypertension rely on a relationship based on a diameter of the central retinal vasculature (CRV) and a tendency towards (a level of) hypertension. The CRV is, however, not visible in retinal images, and it is therefore necessary to calculate or derive an estimate of the diameter of the CRV from the vasculature that is visible in the retinal image. That is, it is necessary to introduce an approximation because such approaches rely on a relationship between the calibres of vessels joining at a branch point. Also, the calibres of vessel segments are combined in a way which is not related to the actual branching visible in the image.

More specifically, the Knudtson method (Knudtson et al., "Revised formulas for summarizing retinal vessel diameters", 2003, Current Eye Research, 27(3), 143-149) has been used to estimate a diameter or width of the hidden CRV. In order to do so, the Knudtson method makes an assumption about a branching configuration of the blood vessels, as this information is unknown because the number of bifurcations in the eye varies considerably from person to person. In particular, the Knudtson method makes use of an empirically derived branching coefficient and applies a branching formula, arbitrarily, to blood vessels in order of descending vessel width, in particular, by using an iterative procedure of pairing a vessel of a largest width with a vessel of a smallest width when determining an estimate of a parent trunk of the two vessels, even though this assumption may not relate to the actual physical branching arrangements of the blood vessels. This approach was used, for example, in U.S. Pat. No. 9,924,867 B2 to iteratively determine an arteriolar-to-venular ratio, AVR, from a ratio of the Central Retinal Artery Equivalent (CRAE) and the Central Retinal Vein Equivalent (CRVE).

Simulations have been conducted by the present inventors in which the branching formula of the Knudtson method was used to determine the CRV (i.e. CRVE or CRAE as described above) applied to (a) a set of blood vessel widths in 100 randomly selected orderings and (b) to the same blood vessel width in the order specified by the Knudtson method. FIG. 1 shows simulation results in a bar chart. In the bar chart, the white bar is indicative of the estimated width of the CRV determined using the Knudtson method (the height of which is not relevant). The black bars in the bar chart are indicative of the frequency with which a particular value is determined as the estimated CRV width when the set of blood vessel widths are ordered using a randomly selected ordering. As is clear from FIG. 1, the estimated CRV width is significantly inconsistent over the 100 randomly selected orderings.

The results shown in FIG. 1 indicate that the actual CRV width may be significantly different from the estimated CRV width, which demonstrates a failing of the Knudtson method. This in turn suggests that there is a potential for lack of accuracy or precision in the use of retinal images to detect or predict hypertension based on a relationship between a level of hypertension and the diameter of the CRV.

There is therefore a need for an improved methodology for an (early) detection of hypertension from retinal images, as well as an (early) determination of levels of hypertension from retinal images.

The present inventors have surprisingly and unexpectedly determined that, instead of relying on a relationship between a level of hypertension and a diameter of the CRV (or values for CRAE or CRVE), it is possible to predict hypertension using retinal images by relying on a direct relationship between measurements of the retinal vasculature visible in the retinal image and a level of hypertension. Therefore, the present inventors have devised a way of determining a level of hypertension without making any estimate or assumptions about the hidden CRV, branching coefficients, vessel equivalents or the like. Accordingly, the possible variations introduced by estimation may be avoided.

In this regard, the present inventors have devised, in accordance with a first example aspect herein, a computer-implemented method for determining a level of hypertension of a person. The method comprises acquiring image data defining a retinal image of a retina of the person that has been captured by a retinal imaging system; processing the image data to identify a plurality of vessel segments present in the retinal image; determining respective widths of vessel segments of at least a subset of the plurality of vessel segments present in the retinal image; and calculating, as a vascular summary metric, at least one average value or median value of the determined widths of the vessel segments present in the retinal image, to determine a level of hypertension by which the person has been affected.

The present inventors have further devised, in accordance with a second example aspect herein, a computer program which, when executed by a computer, causes the computer to perform the method according to the first example aspects herein.

The present inventors of further devised, in accordance with third example aspect herein, an apparatus for determining a level of hypertension of a person, said apparatus comprising an acquiring module, a processing module, a determining module and the calculating module. The acquiring module is configured to acquire image data defining a retinal image of a retina of the person that has been captured by a retinal imaging system. The processing module is configured to process the image data to identify a plurality of vessel segments present in the retinal image. The determining module is configured to determine respective widths of vessel segments of at least a subset of the plurality of vessel segments present in the retinal image. The calculating module is configured to calculate, as a vascular summary metric, at least one average value or median value of the determined widths of the vessel segments present in the retinal image, to determine a level of hypertension by which the person has been affected.

BRIEF DESCRIPTION OF THE DRAWINGS

Embodiments of the invention will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

Figure 2:
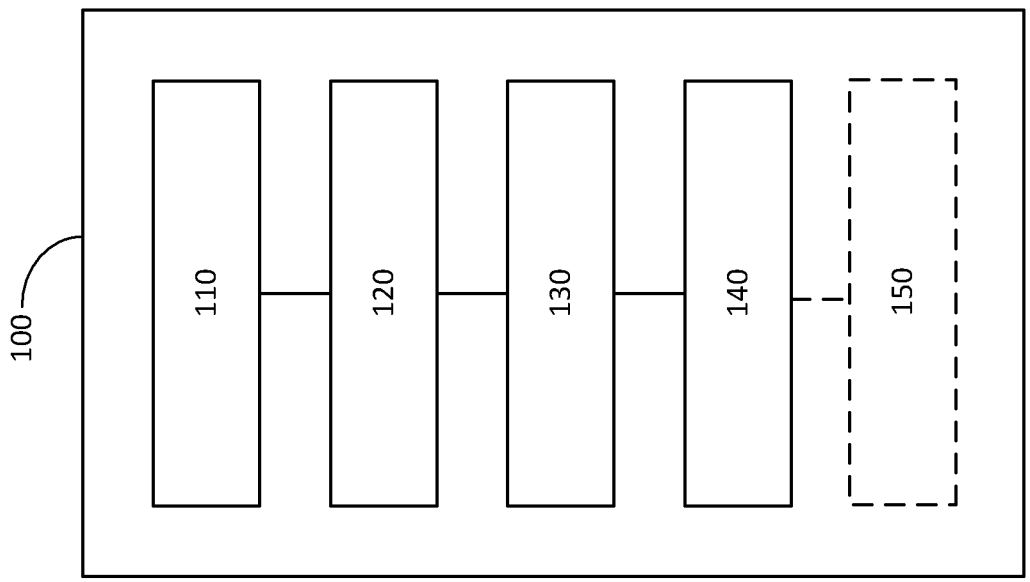
FIG. 2 is a schematic illustration of an apparatus for determining a level of hypertension of a subject such as a person, according to an example embodiment herein.

FIG. 2 is a schematic illustration of an apparatus 100 for determining a level of hypertension of a subject such as, e.g., person, according to an example embodiment herein. The apparatus 100 comprises an acquiring module 110, a processing module 120, a determining module 130, and a calculating module 140. In addition, the apparatus 100 may optionally comprise a display control signal generator 150 (indicated using dashed lines).

Figure 1:
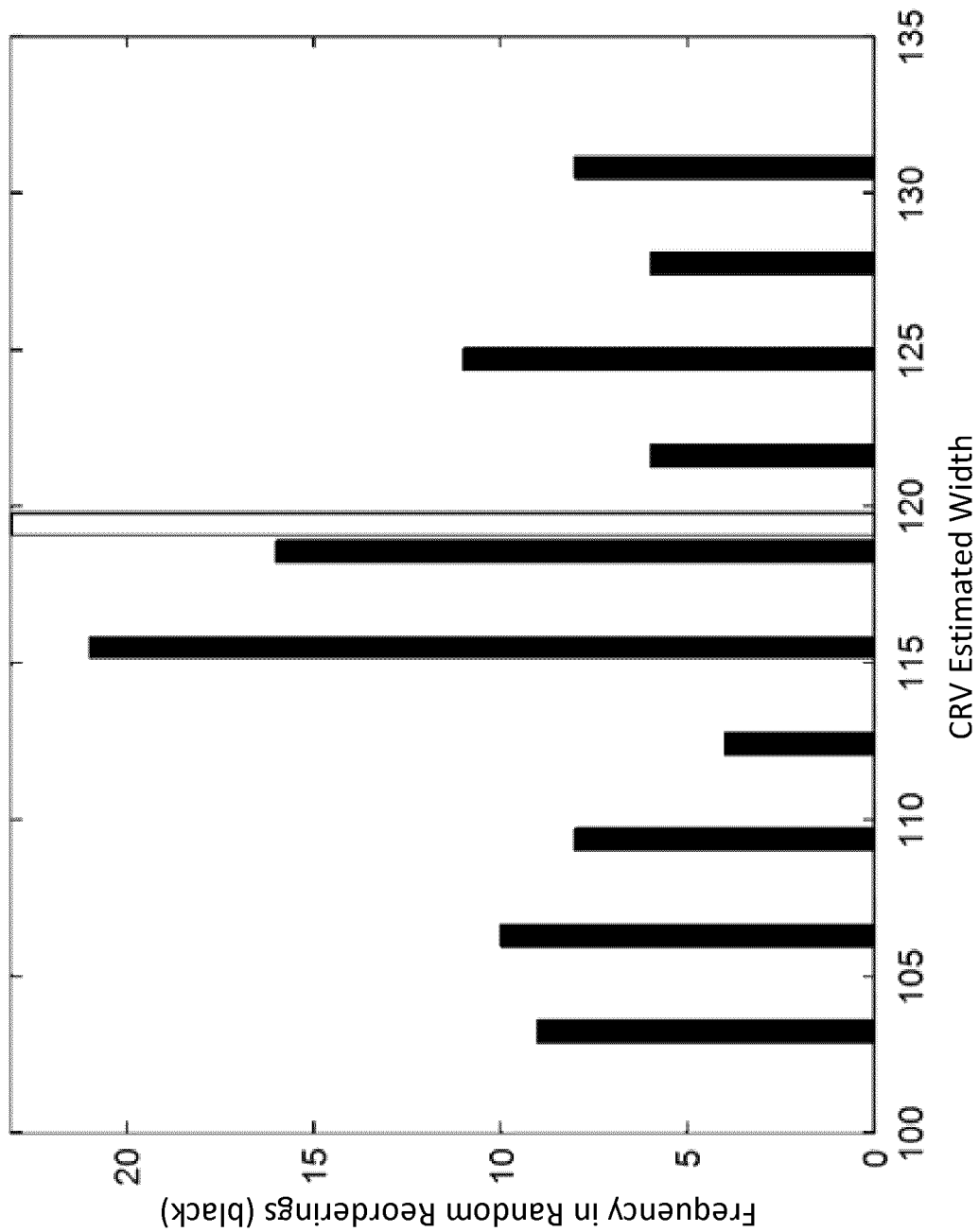
FIG. 1 is a bar chart showing simulation results which indicate that the actual CRV width may be different from the estimated CRV width estimated using the Knudtson method.
Figure 3:
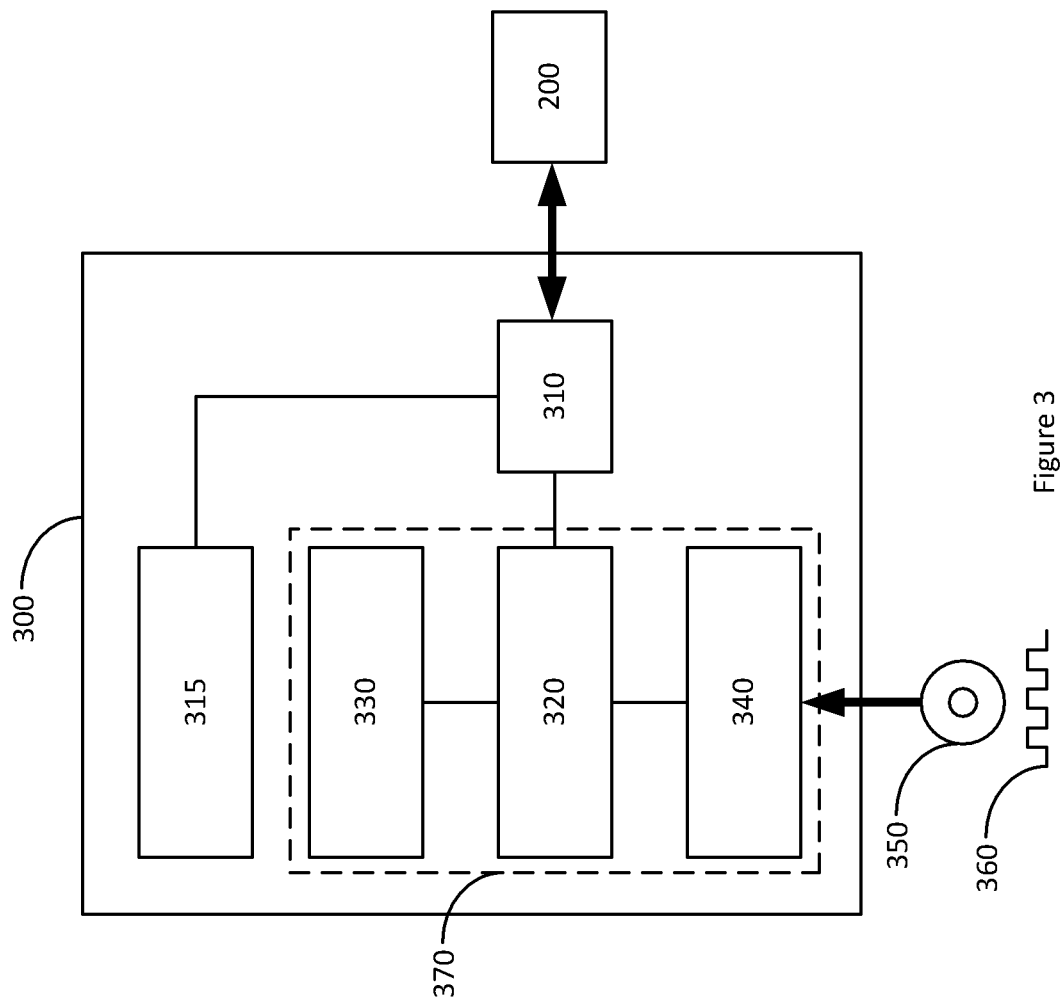
FIG. 3 is a block diagram illustrating an example signal processing hardware configuration of the apparatus of FIG. 2, according to an example embodiment herein.
Figure 5A:
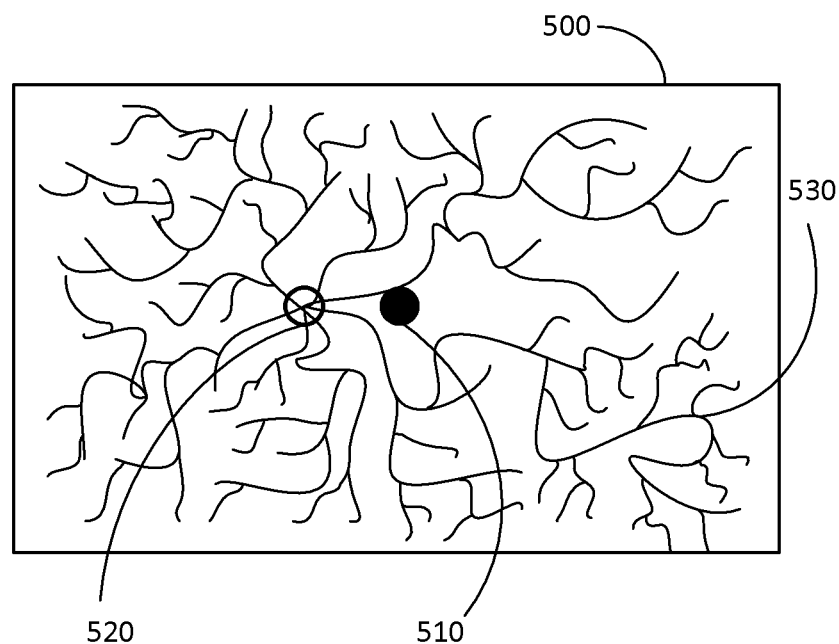
FIG. 5(a) is a schematic illustration of a retinal image of a portion of the retina of a subject captured using a scanning laser ophthalmoscope, SLO, in which the image data defining the retinal image has been processed to locate retinal landmarks, in accordance with an example embodiment herein.

The acquiring module 110 is configured to acquire image data defining a retinal image 500 (as shown in FIG. 5(a)) captured from the person by a retinal imaging system 200 (as shown in FIG. 3). The processing module 120 is configured to process the image data to identify a plurality of vessel segments present in the retinal image. The determining module 130 is configured to determine a width (respective widths) of at least a subset of the plurality of vessel segments. The calculating module 140 is configured to calculate, as a vascular summary metric, at least one of average value or median value of the widths of the subset of the plurality of vessel segments, to determine whether the person has been affected by hypertension and/or a level of hypertension of the person.

The acquiring module 110 is configured to acquire image data defining a retinal image 500 captured from the person (that is, the subject being imaged) by a retinal imaging system 200. The retinal image defined by the acquired image data may be a representation of the retinal fundus, of the retinal fundus features, or of any suitable portion of the retina. From this representation, such as a photograph, retinal fundus features can be explored and measured. The acquired image data may, as in the present example embodiment, define a two-dimensional image, or it may alternatively define a three-dimensional image of the imaged portion of the retina. The received image data may be provided in any suitable format (whether compressed or uncompressed) known to those skilled in the art.

The retinal imaging system 200 may be any ocular imaging system that is suitable for imaging the retina of the eye. The retinal imaging system 200 may, for example, be a fundus camera, or a type of scanning imaging system. By way of example, the retinal imaging system 200 of the present example embodiment is a scanning imaging system in the exemplary form of a scanning laser ophthalmoscope (SLO), which is configured to acquire images of the retina of a subject's eye. The SLO of the present example embodiment is configured to capture Red-Green (RG) reflectance images. In a case, as in the present embodiment, where the retinal imaging system 200 is a scanning laser ophthalmoscope that generates simultaneous red and green images, the red and green images may be combined to give a pseudo-colour image of the retina.

By way of example, green light at a wavelength of 532 nm has a short penetration into the retina and is quickly absorbed by the blood column. Red light at 633 nm is preferentially absorbed by deoxygenated haemoglobin causing veins to appear with greater contrast than arteries. Alternatively, other wavelengths may be used. The retinal imaging system 200 in the exemplary form of a SLO may alternatively or additionally be configured to acquire one or more other types of images, such as, for example, autofluorescence (AF) images or images from other fluorescence modes.

The SLO may, for example, be an ultra-widefield SLO (UWF-SLO) capable of generating an ultra-widefield image of up to 80% of a retinal surface. Each ultra-widefield image may have dimensions of, for example, 4000×4000 pixels with an on-axis resolution of approximately 15.0 µm and represent a stereographic projection of the retinal surface.

Alternatively, the retinal imaging system 200 may be of another imaging modality, for example an optical coherence tomography (OCT) scanner, in which case the image processing techniques described herein are applicable to the tomographic images captured by the OCT scanner. As a further alternative, the retinal imaging system 200 may be a combined SLO-OCT scanner, in which case the image processing techniques described herein are applicable to both the SLO retinal scans and the OCT scans captured by the combined SLO-OCT scanner. The imaging modality of the ocular imaging system may, for example, take one of the many different forms known to those versed in the art, including OCT, colour fundus photography, fluorescein angiography (FA), indocyanine green angiography (ICG) and autofluoresence (AF), among others. By way of further alternative, the retinal imaging system 200 may be configured to perform imaging of tissue oxygenation. Such an imaging modality may be useful for artery and vein (AV) classification based on the difference in the oxygen content of the blood between the arterial blood and the venous blood. Furthermore, the retinal imaging system 200 may be configured to perform speckle analysis which may be used in determining blood flow direction and thus AV classification, as well as possibly vessel classification.

The acquiring module 110 is configured to acquire image data defining the retinal image captured by the retinal imaging system 200 by any suitable means known to those versed in the art. For example, the acquiring module 110 may receive the image data from the retinal imaging system 200 via a direct communication link (which may be provided by any suitable wired or wireless connection, e.g. a Universal Serial Bus (USB) or a Bluetooth™ connection), or an indirect communication link (which may be provided by a network comprising a Local Area Network (LAN), a Wide Area Network (WAN) and/or the Internet). Furthermore, the image data may be acquired by the acquiring module 110 acquiring (e.g. by reading from a storage medium such as a CD or hard disk, or receiving via a network such as the Internet) such image data after it has been captured by the retinal imaging system 200.

Furthermore, the image data may be acquired by the acquiring module 110 (and may furthermore subsequently be processed to determine (a level of) hypertension of the person being imaged, as described below) as this image data is being generated by the retinal imaging system 200, i.e. the image data may be acquired "on the fly", without waiting for the retinal imaging system 200 to finish generating all of the image data that forms the image of the portion of the retina. However, in the present example embodiment, and for the purposes of this description, the acquiring module 110 is configured to acquire all of the image data defining the image of the portion of the retina (the retinal image) before the processing module 120 begins to process this image data.

Alternatively, the acquiring module 110 itself may include a retinal imaging system 200 as described above.

In embodiments like the present illustrated embodiment, where the apparatus 100 comprises a display control signal generator 150, the display control signal generator 150 may be arranged to generate display control signals for controlling a display device (as shown at 315 in FIG. 3), such as an LCD screen or other type of visual display unit, to display at least one of the retinal image, a representation of the identified plurality of vessel segments, representation of the vascular summary metric, and the determination result of whether the person imaged has been affected by hypertension.

FIG. 3 is a block diagram illustrating an example signal processing hardware configuration 300 of the apparatus 100 of FIG. 2, according to an example embodiment herein. The programmable signal processing hardware 300 comprises a communication interface (I/F) 310 for acquiring the image data described above, and, optionally, for outputting display control signals for controlling the display device 315 to display at least one of one of the retinal image, a representation of the identified plurality of vessel segments, representation of the vascular summary metric, and the determination result of whether the person imaged has been affected by hypertension. The signal processing apparatus 300 further comprises a processor (e.g. a Central Processing Unit, CPU, or Graphics Processing Unit, GPU) 320, a working memory 330 (e.g. a random access memory) and an instruction store 340 storing a computer program comprising the computer-readable instructions which, when executed by the processor 320, cause the processor 320 to perform various functions including those of the processing module 120, the determining module 130, the calculating module 140 and, optionally, the display control signal generator 150 (and acquiring module 110 and display device 315) described above.

The instruction store 340 may comprise a ROM (e.g. in the form of an electrically-erasable programmable read-only memory (EEPROM) or flash memory) which is pre-loaded with the computer-readable instructions. Alternatively, the instruction store 340 may comprise a RAM or similar type of memory, and the computer-readable instructions of the computer program can be input thereto from a computer program product, such as a non-transitory, computer-readable storage medium 350 in the form of a CD-ROM, DVD-ROM, etc. or a computer-readable signal 360 carrying the computer-readable instructions. In any case, the computer program, when executed by the processor, causes the processor to execute at least one of the methods for determining a level of hypertension of a person described herein. It should be noted, however, that the apparatus 100 may alternatively be implemented in non-programmable hardware, such as an application-specific integrated circuit (ASIC).

In the present example embodiment, a combination 370 of the hardware components shown in FIG. 3, comprising the processor 320, the working memory 330 and the instruction store 340, is configured to perform functions of the processing module 120, the determining module 130, and the calculating module 140, which functions will now be described in detail below. In embodiments like the present illustrated embodiment, where the apparatus 100 comprises a display control signal generator 150, the functionality of this optional component also be provided by the combination 370 of the hardware components, together with the communication I/F 310.

As will become more apparent from the following description of the operations performed by the apparatus 100 of the present example embodiment, a methodology is provided by which an (early) detection of (a level of) hypertension is provided by an analysis of retinal images without making any estimate or assumption about the hidden central retinal vasculature.

Figure 4:
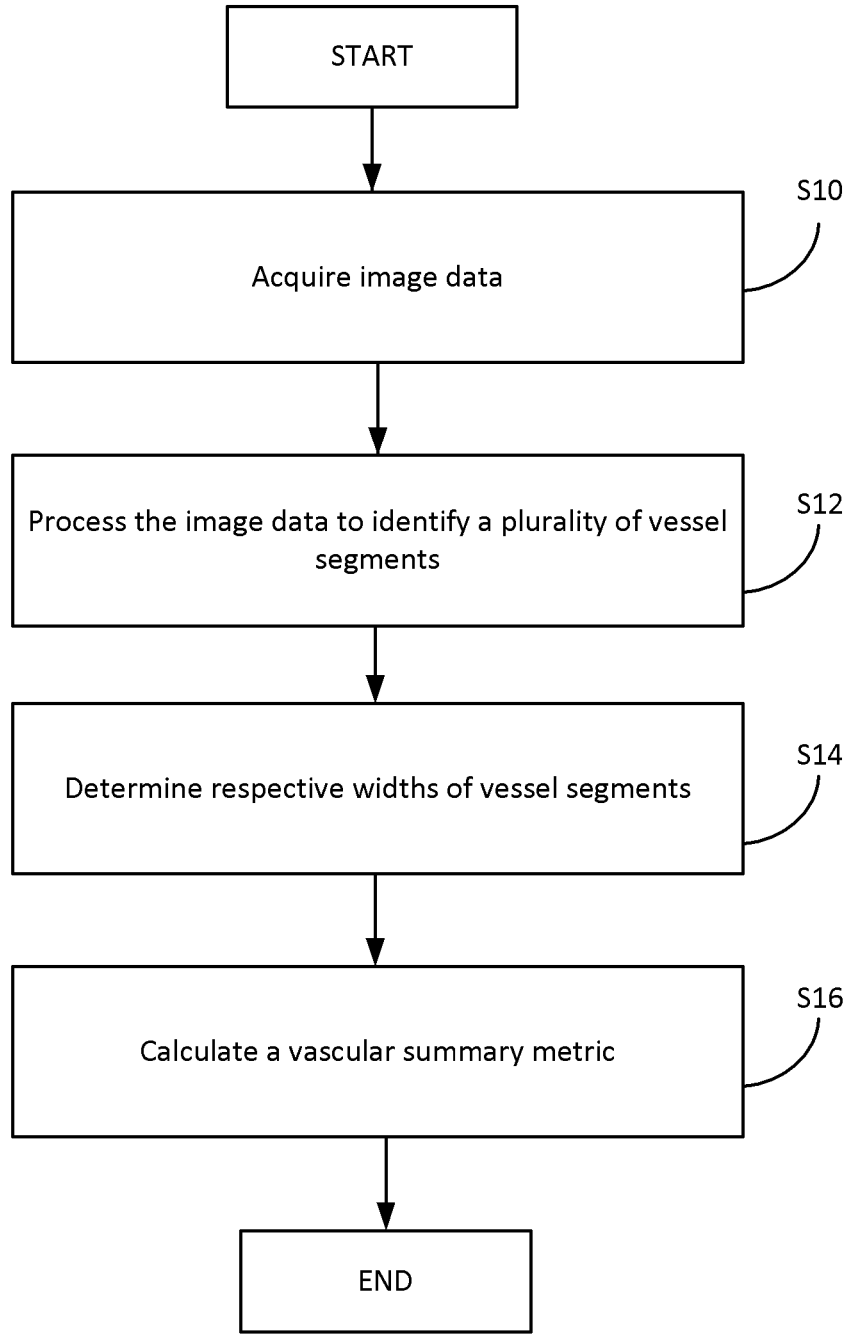
FIG. 4 is a flow diagram illustrating a process by which the apparatus of FIG. 2 processes image data to determine hypertension of a person, in accordance with an example embodiment herein.

FIG. 4 is a flow diagram illustrating a process by which the apparatus 100 of FIG. 2 processes image data to determine hypertension of a subject (e.g., a person), in accordance with an example embodiment herein.

In process step S10 of FIG. 4, the acquiring module 110 acquires image data defining a retinal image captured from the person by a retinal imaging system.

As discussed above, the acquiring module 110 may be considered to acquire the image data defining a retinal image by any suitable means known in the art.

In process step S12 of FIG. 4, the processing module 120 processes the image data to identify a plurality of vessel segments present in the retinal image.

Processing the image data to identify a plurality of vessel segments present in the retinal image may be referred to as vessel segmentation. Vessel segmentation is any method that takes as input image data defining an image, a sub-image, a set of images, a set of sub-images, or a representation of images, including some or the entire original retinal fundus image, and outputs a representation of vessel likelihood and, optionally, a retinal image representation. The representation of vessel likelihood may be, for example, a vessel probability map in which, for each pixel or each group of pixels in the input image data, a probability that that pixel or group of pixels constitutes a vessel is provided. In some embodiments, the representation of vessel likelihood may be combined with a retinal image representation as a single output.

Additionally, the representation of vessel likelihood may be processed using a threshold in order to produce a binary map in which pixels or groups of pixels which have been identified as constituting vessel with a probability that is above a certain threshold have a first value and all other pixels are groups of pixels have a second value. An exemplary binary map is shown in FIG. 6(*d*) and described in detail below.

Furthermore, in a case where processing the image data to identify the plurality of vessel segments comprises pre-processing (that is, processing the image data prior to vessel segmentation) the image data to improve recognition of vessel segments, the output of the pre-processing may be provided as input to the vessel segmentation processing.

The identified plurality of vessel segments may be a plurality of portions of the retinal vasculature (that is retinal veins, arteries and other blood vessels) that may be imaged as part of the retina using the retinal imaging system 300. Each of the plurality of vessel segments may be a uniquely identified portion of the retinal vasculature that can be processed (for example, to determine area, width, location) individually as a distinct unit by the apparatus 100.

The processing of the image data by the processing module 120 to identify the plurality of vessel segments may comprise processing the image data to locate retinal landmarks. A retinal landmark is any retinal anatomical landmark (retinal feature) which is visible or may be identified in a retinal image or other representation of the retina. Retinal landmarks may include at least one of the optic disc, the optic nerve head, fovea and/or the retinal vasculature. Locating of the retinal landmarks may be performed using any method known in the art to locate retinal fundus anatomical landmarks in an image or other representation of the retinal fundus.

By way of example, retinal landmarks may, as in the present example embodiment, be automatically identified and located by the processing module 120 using a computer algorithm. Alternatively, retinal landmarks may be identified and located by manual operation by the user of apparatus 100. By way of non-limiting example, in embodiments like the present embodiment, where the apparatus 100 comprises a display control signal generator 150, the display control signal generator 150 may be arranged to generate display control signals for controlling a display device to display the acquired retinal image on-screen and the retinal features (landmarks) may be identified by the user selecting the retinal features on the displayed retinal image using mouse clicks or any other suitable selection means. Located retinal landmarks may be used for further exploration of retinal features in specified areas of the retinal fundus.

FIG. 5(*a*) is a schematic illustration of a retinal image 500 of a portion of the retina of a subject captured using a scanning laser ophthalmoscope, SLO, in which the image data defining the retinal image has been processed to locate retinal landmarks, in accordance with an example embodiment herein. In the example of FIG. 5(*a*), the acquired image data has been processed to identify the fovea 510, the optic disc 520, and the retinal vasculature 530.

Processing, by the processing module 120, the image data to identify the plurality of vessel segments may, as in the present embodiment, comprise selecting a region of interest and processing the image data to identify a plurality of vessel segments in the selected region of interest.

The selected region of interest may also be referred to as a zone of measurement. The selected region of interest may be the whole retinal image, or a portion of the acquired retinal image. By way of example, the selected region of interest may be a portion of the retinal image in the nasal near periphery. In this region of the retina, vessels are better separated and more distinct than near the optic disc where they frequently cross. Accordingly, it may be possible to more conveniently identify the plurality of vessel segments in this region. Alternatively, the selected region of interest may be any other suitable portion of the retina.

In a case, as in the present example embodiment, where processing the image data to identify a plurality of vessel segments comprises selecting a region of interest and processing the image data to identify a plurality of vessel segments in the selected region of interest, the region of interest may be selected using the located retinal landmarks.

Figure 5B:
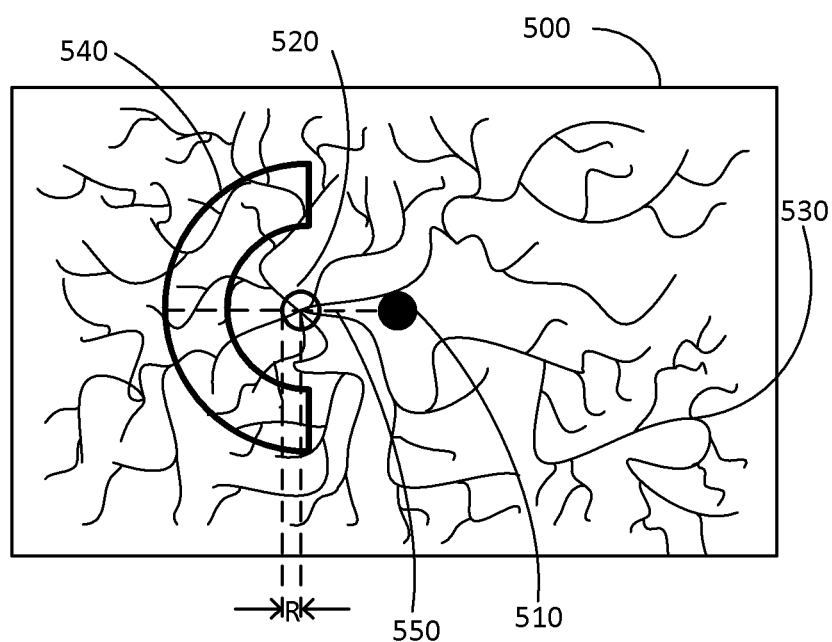
FIG. 5(b) is a schematic illustration of a retinal image of a portion of the retina of a subject captured using a scanning laser ophthalmoscope, SLO, in which a region of interest has been selected, in accordance with an example embodiment herein.

FIG. 5(b) is a schematic illustration of a retinal image 500 of a portion of the retina of a subject captured using an SLO, in which a region of interest 540 has been selected, in accordance with an example embodiment herein. The selected region of interest 540 in this example is a portion of the retinal image in the nasal near periphery.

In the example of FIG. 5(b), the retinal landmarks (the fovea 510, the optic disc 520, and the retinal vasculature 530) were used to establish the region of interest 540 for use in calculation of the vascular summary metric (as discussed below). The region of interest 540 may, as in the present example, be an annular segment subtending 180° nasal to the optic disc 520 and fixed on a line 550 passing through the centre of the fovea 510 and optic disc 520, although this example is non-limiting. The annular segment 540 extends from 3 to 5 optic disc radii R from the optic disc centre. The optic disc radius R may be a fixed value defined as, for example, a number of pixels.

In the example of FIG. 5(b), the region of interest 540 was selected as described above using the identified locations of the fovea 510 and the optic disc 520. Alternatively, the region of interest may be selected in any suitable manner using any combination of located retinal landmarks or by any other suitable means known in the art. By way of example, the region of interest may be selected as a predetermined shape (e.g. an ellipse, rectangle, or annulus) centred on a located retinal landmark (e.g. fovea 510 for the optic disc 520) or as a predetermined portion of the image (e.g. the upper left-hand quarter of the retinal image). Furthermore, the selected region of interest may be of any suitable size.

The processing of the image data by the processing module 120 to identify a plurality of vessel segments may comprise processing the image data to improve recognition of vessel segments.

By way of example, processing the image data to improve recognition of vessel segments may comprise at least one of:
- pre-processing the image data using an adaptive histogram equalisation technique and/or using a morphological image crossing technique;
- enhancing the image data or the pre-processed image data in order to aid detection of retinal features using Hessian filtering;
- creating the vessel segments by splitting a segmented vascular network; and/or
- cleaning the plurality of vessel segments by removing disconnected regions, branches, and offshoots that are unlikely to be the vessel segments.

Image pre-processing may include any method that takes, as input, image data defining a retinal fundus image or portion thereof (such as, for example retinal image 500), and which outputs an image or series of images that is likely to aid detection of retinal features such as the retinal vasculature.

Figure 6A:
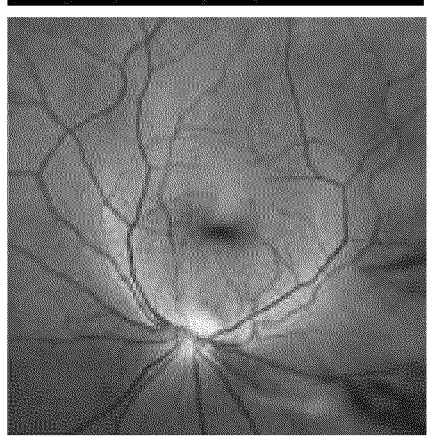
FIGS. 6(a) to 6(d) show retinal images, in which the image data defining the retinal images has been processed to improve recognition of vessel segments, in accordance with an example embodiment herein.
Figure 6B:
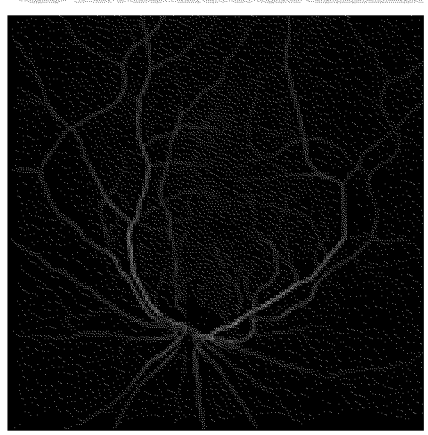

Image pre-processing may include using an adaptive histogram equalisation technique, in one example embodiment herein. Adaptive histogram equalization techniques improve contrast in images by computing multiple histograms, each corresponding to a distinct section of the image, and using them to redistribute the lightness values of the image. Adaptive histogram equalization techniques are suitable for improving the local contrast and enhancing the definitions of edges in each region of an image. By way of example, in an example case, as in the present embodiment, where the retinal imaging system 200 generates simultaneous red and green images, image data defining the green image plane may be pre-processed using an adaptive histogram equalisation technique to remove background variance across the image, as shown in FIG. 6(a). Alternatively, an adaptive histogram equalisation technique may be applied to image data defining the red image plane, to any other suitable colour image plane, or to the acquired image data defining the retinal image or portion thereof.

Additionally or alternatively, image pre-processing may include removing background noise while preserving the retinal vasculature by using morphological image processing techniques. Morphological image processing techniques test an image with a small shape or template called a structuring element. The structuring element is positioned at all possible locations in the image and it is compared with the corresponding neighbourhood of pixels. A morphological image processing technique creates a new image in which, in the case of a grey scale image, each pixel has, for example, a maximum or minimum value of the pixels within the boundary of the structuring element and, in the case of a binary image, each pixel has a non-zero value only if the test (for example, of whether the structuring element "fits" within the neighbourhood or intersects the neighbourhood) is successful at that location in the input image. By way of example, in the example of FIG. 6(b), morphological image processing techniques of opening and closing using a rotating linear structuring element of dimension 1×17 pixels were applied to the acquired image data. By way of alternative, the structuring element may be of any suitable size or shape.

Processing the image data to improve recognition of vessel segments may include performing vessel enhancement. Vessel enhancement is any method that takes as input image data defining a retinal fundus image or a portion thereof, or other representation of the retinal fundus image, such as one that has been pre-processed, and outputs an image where retinal features have been enhanced, such as the retinal vasculature or any of the retinal landmarks discussed above. This may be to aid detection of retinal features for segmentation or measurement.

Figure 6C:
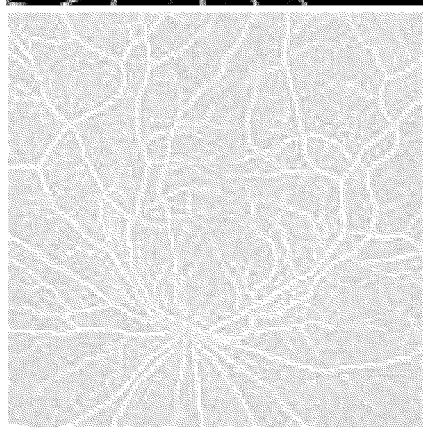
Figure 6D:
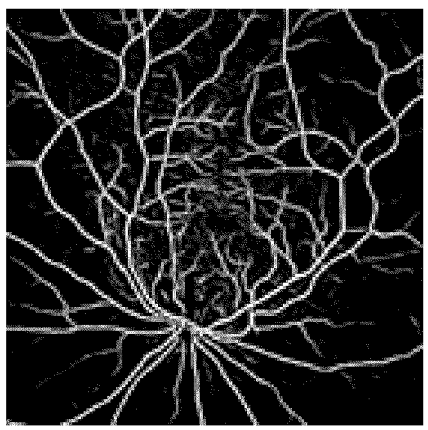
Figure 7A:
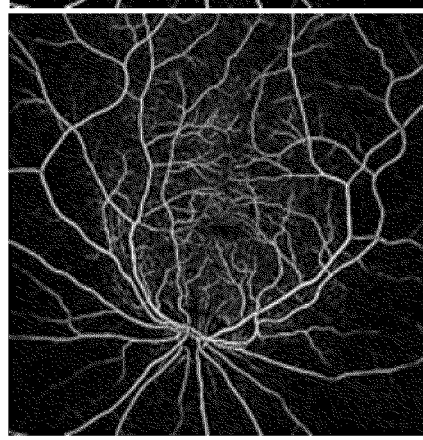
FIGS. 7(a) to 7(d) show a retinal image, in which the image data defining the retinal image has been processed to improve recognition of vessel segments by enhancing the image data in order to aid detection retinal features using Hessian filtering, in accordance with an example embodiment herein.
Figure 7B:
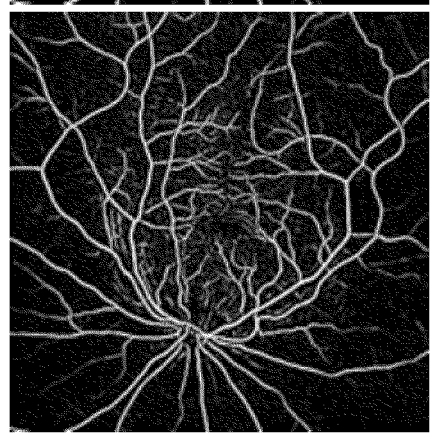
Figure 7C:
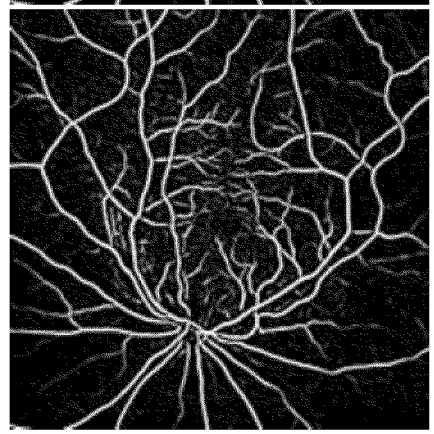
Figure 7D:
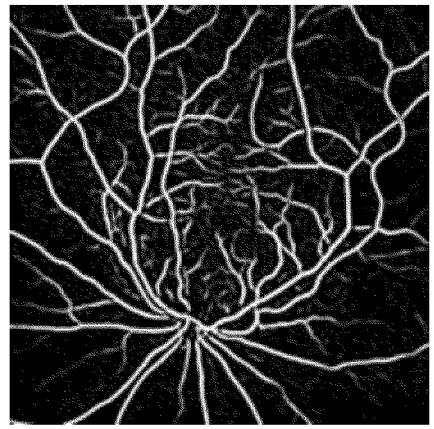

By way of example, in the example of FIGS. 6(c) and 7(a) to 7(d), Hessian filtering has been applied to a retinal image to generate the vessel enhancement parameter maps. Hessian filtering was performed at four scales (e.g., 3, 7, 11, 15 pixels) to enhance vessels of different calibre, as shown in FIGS. 7(a) to 7(d), respectively. Optionally, Hessian processing steps may, as in the present embodiment, also be used to encode vessel direction information into an additional parameter map. An exemplary vessel direction encoding map is shown in FIG. 6(c). These five parameter maps (that is, the four vessel enhancement parameter maps and the vessel direction information parameter map) may then be used to automatically segment the retinal vasculature.

By way of alternative, vessel enhancement may include performing Hessian filtering at any number of scales, and at any the scales discussed above (i.e. 3, 7, 11, 15 pixels) and any other suitable scale. Furthermore, vessel enhancement may alternatively or additionally include any other suitable filtering techniques known in the art.

Processing the image data to improve recognition of vessel segments may also include performing such processing after the plurality of vessel segments has been identified. By way of example, processing the image data to improve recognition of vessel segments may include cleaning the plurality of vessel segments by removing disconnected regions, branches, and offshoots (spurs) that are unlikely to be the vessel segments. Such methods may be referred to as vessel cleaning. In a case where the representation of vessel likelihood is processed using a threshold in order to produce a binary map (such as that shown in FIG. 6(d)), vessel cleaning methods may be applied to the binary map. By way of example, regions with less than 50 pixels, and spur pixels may, as in the present embodiment, be removed from the representation of vessel likelihood or binary map.

In order to perform vessel segmentation, in some embodiments, such as the present embodiment, the processing module 120 may process the image data to identify the plurality of vessel segments based on a classification algorithm trained on image data defining retinal images of a plurality of subjects.

Figure 8:
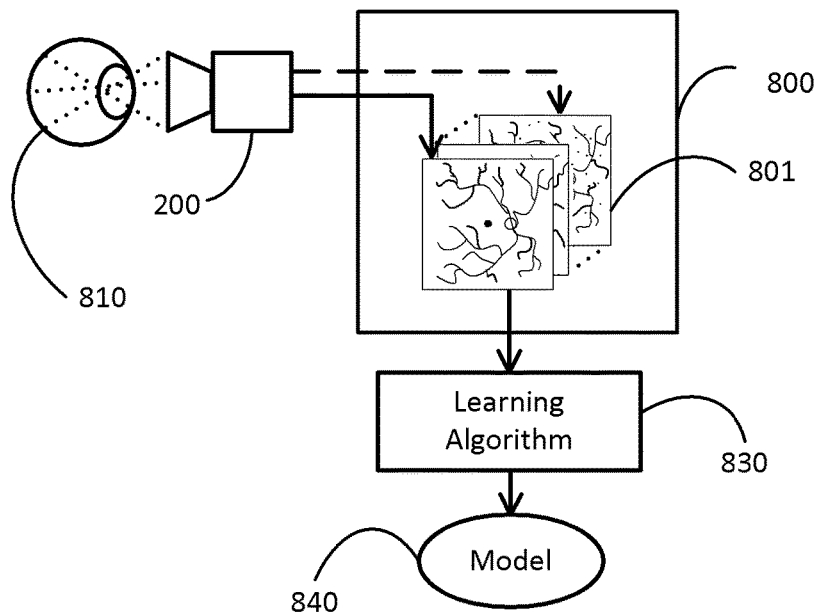
FIG. 8 is a schematic illustration showing how a classification algorithm may be trained on image data defining retinal images of a plurality of subjects, in accordance with an example embodiment herein.

FIG. 8 is a schematic illustration showing how a classification algorithm 830 may be trained on image data 801 defining retinal images of a plurality of subjects, in accordance with an example embodiment herein. In the example of FIG. 8, the images defined by image data 801 are images of a portion of the retina of a plurality of subjects captured using an SLO but may be any form of retinal image captured using any suitable ocular imaging system. In particular, image data 801 defines images of the retina in which the retinal vasculature is visible or can be identified. The classification algorithm 830 is configured to learn from, and make predictions based on input data by building a model 840 from an example training set 800 of input data, comprising the image data 801 defining images of the retina.

The classification algorithm 830 may, as in the present embodiment, be a supervised learning algorithm. In embodiments where the classification algorithm 830 is a supervised learning algorithm (such as a neural network, a support vector machine or an evolutionary algorithm, for example), each example image in the example training set 800 consists of input image data defining an image of the portion of the retina in which each pixel or group of pixels has an associated desired output value indicating whether the pixel constitutes a vessel or not. By way of example, the desired output value may be one in the case in which the pixel constitutes a vessel and zero otherwise. Alternatively, any other suitable pair of binary values may be used. The supervised learning algorithm 830 analyses the image data in the example training set 800 and produces a model 840, which can be used to classify pixels or groups of pixels in new unseen image data defining an image of the portion of the retina as constituting a vessel or not.

The supervised learning algorithm 830 may, as in the present example embodiment, be a neural network, such as for example a convolutional neural network. Convolutional neural networks are particularly suitable to image and video recognition tasks. Neural networks automatically generate identifying characteristics by processing the input data, such as the image data in the example training set 800, without any prior knowledge.

Figure 9:
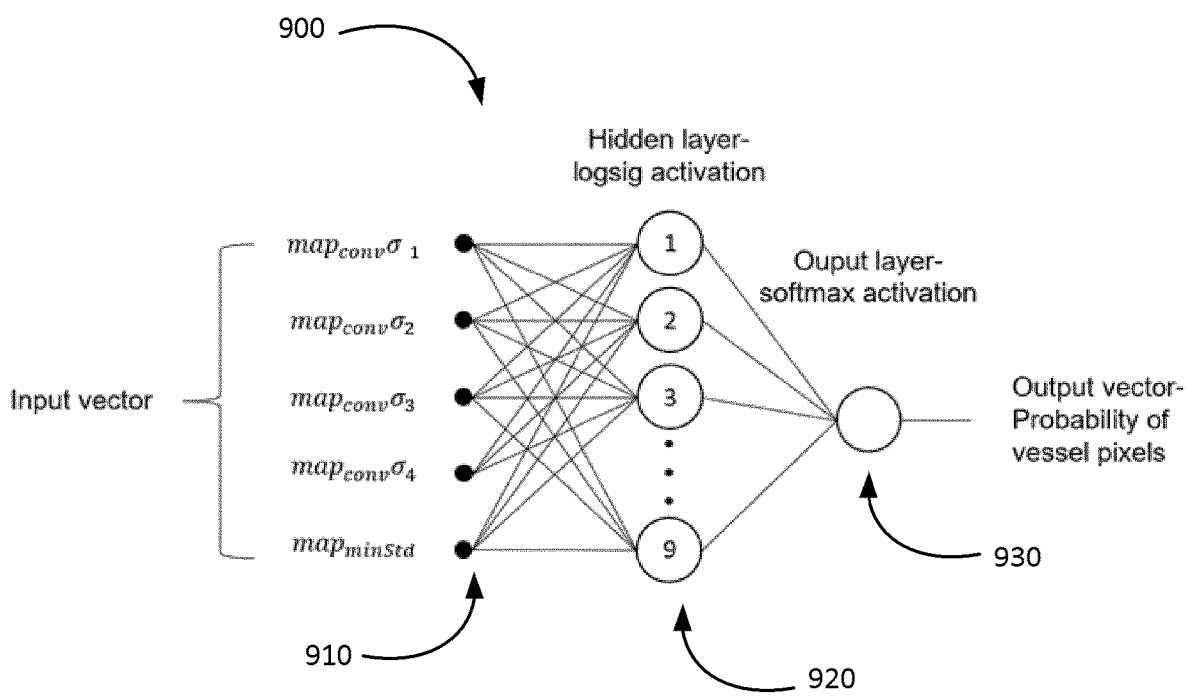
FIG. 9 is a schematic illustration of a specific example of neural network comprising artificial neurons and an input layer, a hidden layer, and an output layer.

FIG. 9 is a schematic illustration of one specific, non-limiting example of neural network 900 that may be used for the learning algorithm 830, wherein the neural network 900 comprises artificial neurons and an input layer 910, a hidden layer 920, and an output layer 930 (of course, in other example embodiments, other neural network structures can be used instead). In the example of FIG. 9, the neural network 900 comprises five input nodes 910 corresponding to five input parameters (e.g. a retinal image such as image 500, a part thereof and/or a processed retinal image, such as any of the processed retinal images in FIGS. 6(a) to 6(d) and 7(a) to 7(d)) which make up an input vector. The neural network 900 may, as in the example of FIG. 9, be trained using, for example and without limitation, a cross entropy loss function which quantifies the difference between network predictions and the training class. The neural network 900 of the example of FIG. 9 contains one hidden layer 920 with 12 neurons and logsig activations. A softmax activation maybe used for the output layer 930 to provide a probability of a pixel belonging to a vessel, in one example embodiment herein.

The output of the neural network, once it has been applied to each pixel of the input image data, is a vessel probability map. A threshold may then be applied to the vessel probability map to produce a binary map. In the case of the example of FIG. 9, a hysteresis threshold technique may be used, that applies a dual threshold to the vessel probability map. In this case, a value used for an upper threshold may be, for example, 0.65 (that is, any pixel above this value is considered a vessel pixel). A lower threshold may then be used to retain pixels (of value greater than, for example, 0.5) that touch vessel pixels.

Accordingly, the output of process step S12 of FIG. 4, is a representation of vessel likelihood, provided by the processing module 120, that identifies a plurality of vessel segments present in the retinal image.

In process step S14 of FIG. 4, the determining module 130 determines a width of at least a subset of the plurality of vessel segments.

Determining the width of at least a subset of the plurality of vessel segments may comprise any suitable method that can be used to determine or estimate the width of vessels, such as by, for example, measuring a cross-section between retinal vessel boundaries (although this example is not limiting). The determining module 130 may determine a width of each of the plurality of vessel segments identified by the processing module 120, or a subset thereof.

In a case where the determining module 130 determines the width of a subset of the plurality of vessel segments, the subset may be selected in any suitable manner. For example, in a case in which a plurality of vessel segments have been identified in the whole retinal image, a region of interest may subsequently be selected and the determining module 130 may be configured to determine a width of each of the plurality of vessel segments in the region of interest only. Alternatively, by way of further example, determining the width of at least a subset of the plurality of vessel segments may comprise determining the width of each identified vessel segments which exceeds a certain threshold with regard to, for example, size and/or length. By way of non-limiting example, in an exemplary embodiment, for each vessel segment whose skeleton contained ≥25 pixels (that is, for which the area of the vessel segment is greater than or equal to 25 pixels), the determining module 130 estimates the calibre of the vessel segment, in micrometres, as the average distance between parallel splines automatically fitted to the detected vessel edges.

Determining the width of at least a subset of the plurality of vessel segments may, as in the present embodiment, comprise shortening the vessel segments such that the vessel segments are likely to have uniform width. Such a shortening process may be referred to as creation of vessel segments.

Creation of vessel segments may comprise any suitable method that further splits the segmented retinal vasculature into sub-segments (or portions or components) which are short enough to be likely to have uniform width along the entire length of the sub-segment. Additionally or alternatively, the creation of vessel segments may comprise splitting the segmented retinal vasculature into sub-segments which are likely to have few or no branches, and/or which are likely to consist entirely of pixels from the same vessel (that is, containing no vascular crossovers).

Figure 10A:
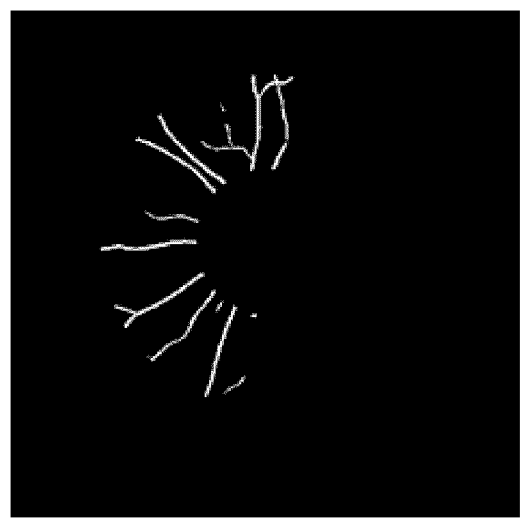
FIGS. 10(a) to 10(c) show images illustrating a process by which a plurality of vessel segments is identified in a region of interest, in accordance with an example embodiment herein.
Figure 10B:
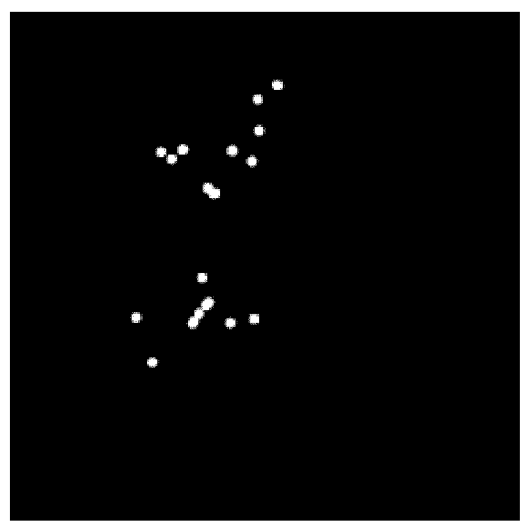
Figure 10C:

FIGS. 10(a) to 10(c) illustrate a process by which a plurality of vessel segments is identified in a region of interest, in accordance with an example embodiment herein. In the example of FIGS. 10(a) to 10(c), the vessel binary map is clipped within a dilation of the region of the interest (in this case, region of interest 540 of FIG. 5(b) ±15% of the zone outer and inner radii, respectively) as shown in FIG. 10(a). In the example of FIG. 10(a), for the outer radius this was 5×60×1.15=345 pixels, and for the inner radius this was 3×60×0.85=153 pixels. The dilation may be included to mitigate for junctions, otherwise not identified, at the edge of the region-of-interest.

Next, the morphological skeleton of the clipped vessel segmentation is generated, and from this crossings and bifurcations are identified. At each crossing or bifurcation, pixels within a disc of radius 10 pixels are masked, as shown in FIG. 10(b), in order to remove the crossings and bifurcations. Only distinct vessel segments remained. As a final step, the vessel segment map is clipped to the undilated region-of-interest (i.e. by way of non-limiting example, for inner radius 3×60=180 pixels, and outer radius 5×60=300 pixels) as shown in FIG. 10(c). The distinct vessel segments in the undilated region of interest may, in some example embodiments, serve as the identified plurality of vessel segments.

The determining module 130 may, as in the present example embodiment, be configured to determine the width of at least a subset of the plurality of vessel segments by measuring the width (calibre or diameter) of each of the identified plurality of vessel segments in the retinal image and converting the measured width into real units.

Conversion of width or calibre to real measurement units may include performing any suitable method that can be used to convert measurements made on a representation of the retina, such as the retinal image defined by the image data acquired by the acquiring module 110, to real units, for example metric units such as nanometres, micrometres and/or millimetres. In the present exemplary embodiment, pixel estimates of vascular width are converted to micrometres using a pixel to micrometre scale that may vary with position in the image.

In process step S16 of FIG. 4, the calculating module 140 calculates, as a vascular summary metric, at least one average value or median value of the determined widths of vessel segments present in the retinal image, to determine a level of hypertension by which the person has been affected. As compared to the Knudtson method described above, the calculation of this vascular summary metric is a non-iterative calculation which, in particular, does not rely on estimates or assumptions about the hidden CRV, branching coefficients, vessel equivalents or the like, and is thus based only on the directly measurable widths.

Calculation of the vascular summary metric, by the calculating module 140, may comprise any suitable method that can be used to summarize vessel segment width measurements. In particular, the vascular summary metric may be a single metric or value that summarises (that is, provides an overview or summary of some property of) the widths of the subset of the plurality of vessel segments for which widths were determined by the determining module 130.

In some embodiments, the calculating module 140 may be configured to categorise each of the plurality of the vessel segments as an artery or non-artery as part of calculating vascular summary metric. In such embodiments, the calculating module 140 may be further configured to calculate, as the vascular summary metric an average venule width and an average arterial width and/or a median venule width and a median arterial width, wherein the average venule width or median venule width may be calculated using the widths of the vessel segments classified as non-artery.

Categorising each of the plurality of vessel segments as an artery or non-artery (which may, in effect allow each of the plurality of blood vessels to be classified as veins and arteries) may be referred to as artery vein classification. Artery vein classification may include any method that takes as input a set of images, or sub-images, or representation of images (including some or all of the original retinal fundus image, the output of the pre-processing (if performed), the output of the vessel enhancement step (if performed), the representation of vessel likelihood, and/or the binary map) and outputs a representation of retinal vessels and a representation of their class, i.e., artery or non-artery (vein).

In order to perform artery vein classification, in some embodiments, such as the present embodiment, the calculating module 140 may further process the image data using a supervised learning algorithm trained on image data defining retinal images of a plurality of subjects. This supervised learning algorithm may, as in the present example embodiment, be a neural network (such as for example a convolutional neural network) and may operate in a manner similar to the classification algorithms described above in relation to process step S14 of FIG. 4.

Figure 11:
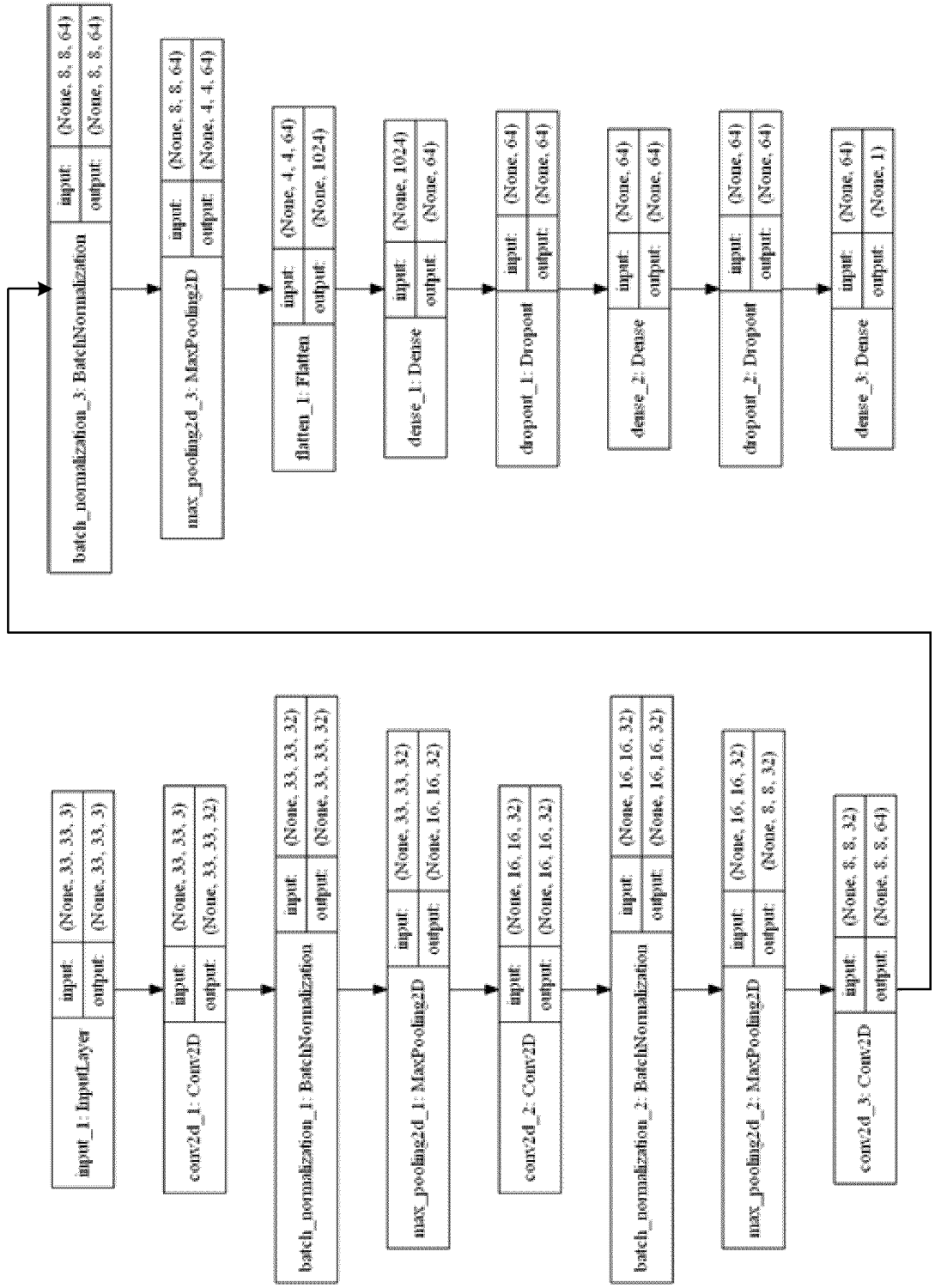
FIG. 11 is a schematic illustration of a convolutional neural network for use in categorising each of the plurality of the vessel segments as an artery or non-artery, in accordance with an example embodiment herein.

By way of non-limiting example, FIG. 11 is a schematic illustration of a convolutional neural network that may be used in categorising each of the plurality of the vessel segments as arteries and non-arteries (and therefore, classified as a vein), in accordance with an example embodiment herein. In the example of FIG. 11, a convolutional neural network (CNN) was trained to classify image patches with 65×65 pixels as containing an artery or a vein. An image patch (65×65 pixels) surrounding each pixel of each vessel segment centreline was supplied to the network. The output of the convolutional neural network is a probability of the patch being of class artery. By inputting each patch of the image to the neural network, an average probability for each vessel segment may be found. A segment may then be classed as artery if the average probability was, for example, greater than or equal to 0.5 and as vein if the average probability was less than 0.5. FIG. 11 illustrates, in detail, the function of each of the layers of the convolutional neural network as well as their inputs and outputs.

By way of alternative, artery vein classification may be performed manually by the user of apparatus 100. By way of non-limiting example, in embodiments like the present embodiment, where the apparatus 100 comprises a display control signal generator 150, the display control signal generator 150 may be arranged to generate display control signals for controlling a display device to display the representation of vessel likelihood produced by the processing unit 120, or a binary map of the retinal vasculature on-screen and vessel segments constituting arteries may be identified by the user selecting the vessel segments on the displayed image using mouse clicks or any other suitable selection means.

The calculating module 140 may be configured to calculate the vascular summary metric in any suitable manner. By way of example, calculating module 140 may be configured to calculate the vascular summary metric by calculating the ratio of the average arterial width to the average venule width.

The ratio of the average arterial width to the average venule width may also be referred to as artery-vein ratio (AVR), but is not a ratio based on CRAE and CRVE as in the Knudtson method which is based on additional estimations or assumptions about the hidden CRV, branching coefficients, vessel equivalents or the like. The present AVR is a morphometric parameter of retinal vessels and may provide more accurate results than, for example, a mean arterial width.

Alternatively, the vascular summary metric calculated by the calculating module 140 may be any one of the average vascular width, the median vascular width, or any other suitable metric. Furthermore, in a case, as in the present embodiment, in which the plurality of the vessel segments is categorised as veins and arteries, the vascular summary metric may be calculated as any one of the ratio of median arterial width to median venule width, the average or median artery width, the average or median vein width, or any other suitable metric.

In some embodiments, calculating the vascular summary metric by the calculating module 140 may comprise selecting a reduced subset of the subset of the plurality of vessel segments for which the widths have been determined; and calculating the vascular summary metric based on the widths of the selected reduced subset of the plurality of vessel segments.

Selecting the reduced subset of the plurality of vessel segments for which widths of those segments have been determined may be referred to as vessel segment selection. Vessel segment selection may include any method that can be used to select vessel segments for further measurement. By way of example, in embodiments in which each of the plurality of vessel segments has been categorised as veins or arteries, selecting the reduced subset of the plurality of vessel segments may comprise selecting, from among the vessel segments categorised as veins, a predetermined number of the widest vessel segments and selecting, from among the vessel segments categorised as arteries, a second predetermined number of the widest vessel segments.

By way of particular example, in the present embodiment, of the segments classified as artery, the three widest were selected by the calculating module 140 and, of the segments classified as vein, the three widest were selected. Alternatively, any suitable number of veins and/or arteries may be selected. By way of further alternative, a subset comprising a predetermined number (for example, three or any other number) of the widest vessel segments may be selected from among the subset of the plurality of vessel segments for which the width of each segment was determined. In a case in which fewer vessel segments or fewer arteries and vein segments than the predetermined number were available, all of the available vessel segments or artery and vein segments may be selected.

Alternatively, instead of performing vessel segment selection based on vessel segment width, vessel segment selection may be performed based on the branching structure of the vasculature or based on a width histogram or by any other suitable means.

In some embodiments, the calculating module 140 may be configured to determine whether a retinal vasculature has been affected by hypertension by comparing the vascular summary metric to a predetermined threshold. That is, calculating module 140 may determine a medical risk indication.

A medical risk indication is any suitable indication of medical risk or for therapy guidance or generation of a normative database. By way of example, in embodiments in which a threshold is applied to the vascular summary metric (for example, an AVR), the medical risk indication may be an indication as to whether the person is considered normotensive or hypertensive. For example, subjects with an AVR that is less than the threshold may be classified as normotensive, and subjects with an AVR that is equal to or greater than the threshold may be classified as hypertensive.

Figure 12:
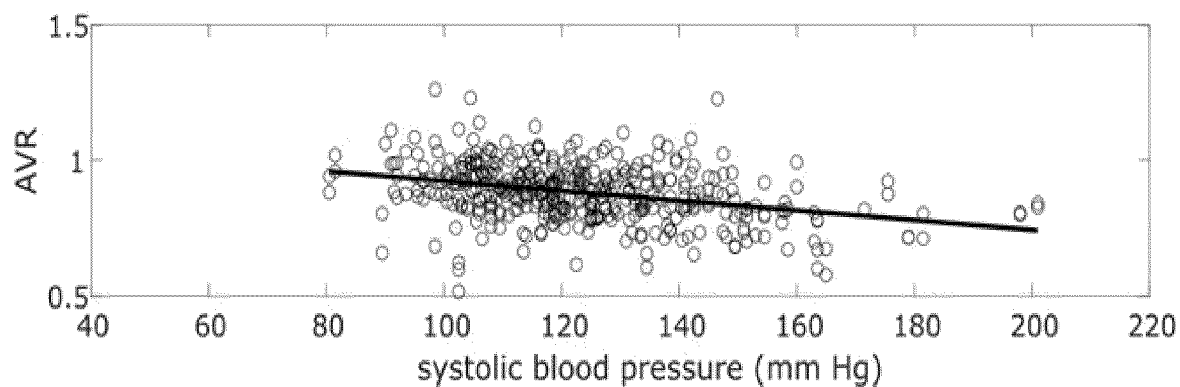
FIG. 12 is a graph of artery vein ratio (AVR) plotted against systolic blood pressure (mm Hg) in which a linear relationship between AVR and systolic blood pressure may be observed.

FIG. 12 is a graph of artery vein ratio (AVR), as defined above, plotted against systolic blood pressure (mm Hg) in which a linear relationship between AVR (ratio of the average arterial width to average venal width) and systolic blood pressure may be observed. In particular, a reduction in AVR with increasing blood pressure can be observed. This demonstrates the surprising capability to determine a level of hypertension by which the person has been affected directly from AVR (as defined above) and without the need to refer to assumptions about a branching configuration of the blood vessels as required in the Knudtson method.

Figure 13:
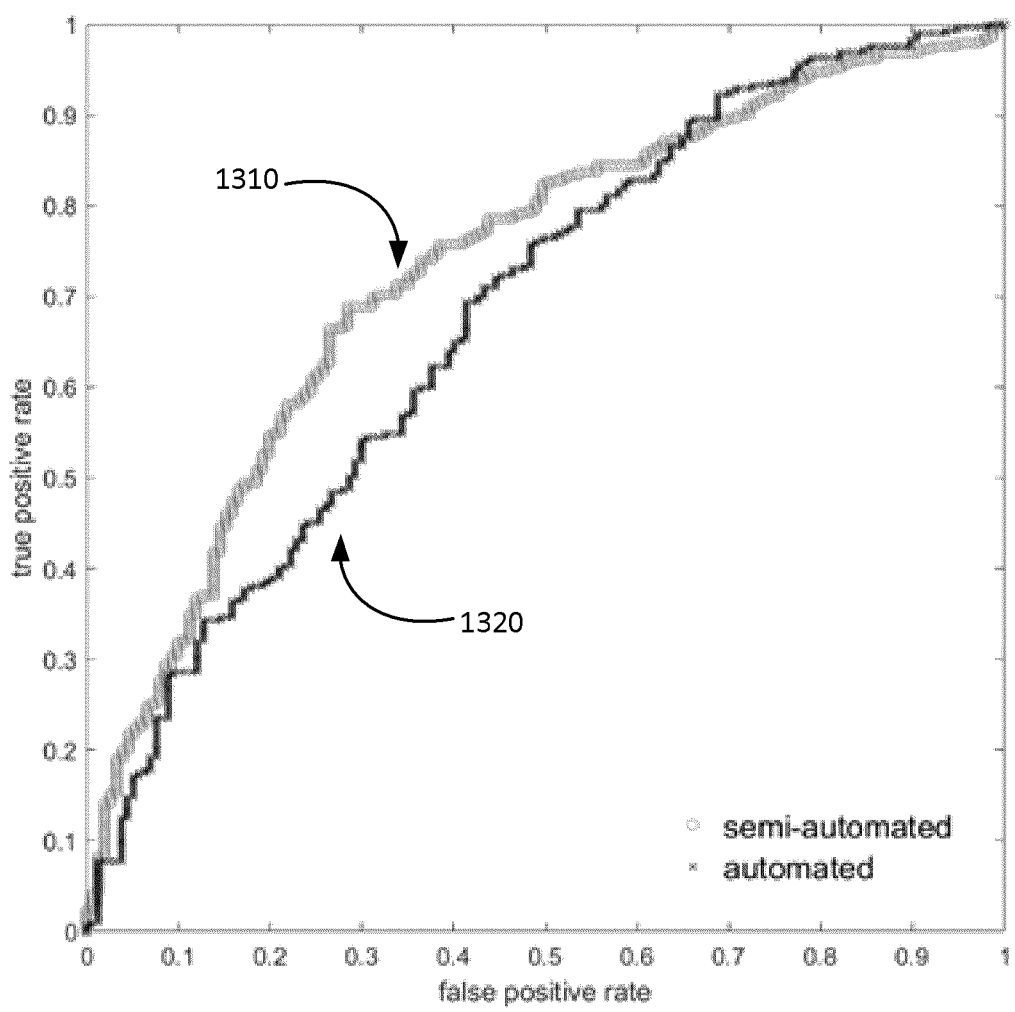
FIG. 13 shows an area under receiver operator curve (AUC) for semi-automated and automated hypertension classification for the left eye using AVR to classify hypertensive individuals.

These results were derived from the analysis of 460 subjects (aged 50-59 years; mean age of 54.6±2.9 years; 259 (56.3%) females). The number of study subjects categorised as hypertensive from their clinical blood pressure measurements was 151 (32.8%), of which 57 (37.7%) were female. A linear relationship between AVR and systolic blood pressure was observed, as shown in FIG. 13. In particular, there was a reduction in AVR with increasing blood pressure ($R2=0.118$, $p<0.005$).

The results for fully- and semi-automated AVR analysis for hypertension classification are presented in Table 1, where area under the receiver operator curve (AUC) is used to assess performance for left and right eyes and for using different numbers of vessel segments in the AVR calculation: AVR_3 (up to 3 segments); and AVR_m (the widest artery and vein segments). Also given is the percentage of subjects from the cohort used (n). The left eye gives superior performance for both semi-automated (0.73) and fully-automated (0.69) methods. For the fully-automated method, the percentage of subjects used was 94% (432/460), compared to 99% (455/460) for the semi-automated method.

TABLE 1

| Method | Left eye | | | Right eye | | |
|---|---|---|---|---|---|---|
| | AVR_3 | AVR_m | n (% of 460) | AVR_3 | AVR_m | n (% of 460) |
| Semi-automated | 0.73 | 0.68 | 99 | 0.64 | 0.63 | 99 |
| Automated | 0.68 | 0.69 | 94 | 0.66 | 0.62 | 97 |

FIG. 13 shows an area under receiver operator curve (AUC) for semi-automated 1310 and automated 1320 hypertension classification for the left eye using AVR to classify hypertensive individuals as described above. Semi-automated results describes results in which artery vein classification is performed manually.

The above results were obtained from combined red-green images captured by an ultra-widefield SLO, having green light at a wavelength of 532 nm and red light at a wavelength of 633 nm. Each ultra-widefield image had dimensions 4000×4000 pixels with an on-axis resolution of approximately 15.0 μm and represented a stereographic projection of the retinal surface. In determining the AVR, a region of interest, as described above in relation to FIG. 5(b) was used.

The images were pre-processed using an adaptive histogram equalisation technique, morphological image processing techniques, and hessian filtering performed at four scales, as discussed above in relation to FIGS. 6(a) to 6(d) and 7(a) to 7(d). A representation of vessel likelihood was obtained using a neural network as described above in relation to FIG. 10 and processed with a hysteresis threshold technique to produce a binary map. The value used for the upper threshold is 0.65, that is, any pixel above this value was considered a vessel pixel. A lower threshold was used to retain pixels (of value greater than 0.5) that touch vessel pixels.

The segmented vessels were then cleaned by removing regions with less than 50 pixels and spur pixels. Furthermore, the vessel binary map was clipped within a dilation of the region of the interest, ±15% of the zone outer and inner radii, respectively. For the outer radius this was 5×60× 1.15=345 pixels, and for the inner radius this was 3×60× 0.85=153 pixels. The dilation was included to mitigate for junctions, otherwise not identified, at the edge of the region-of-interest. Next, the morphological skeleton of the clipped vessel segmentation was generated, and from this crossings and bifurcations were identified. At each crossing or bifurcation, pixels within a disc of radius 10 pixels were masked so that only distinct vessel segments remained. As a final step, the vessel segment map was clipped to the undilated region-of-interest i.e. for inner radius 3×60=180 pixels, and outer radius 5×60=300 pixels.

Then, for each segment whose skeleton contained >25 pixels, the calibre, in micrometres, was estimated as the average distance between parallel splines automatically fitted to the detected vessel edges and pixel estimates of vascular calibre were converted to microns using a pixel to micron scale that varied with position in the image. A convolutional neural network (CNN) was then trained to classify image patches as containing artery or vein, as described above in relation to FIG. 12. Artery vein classification was also performed manually (see semi-automated method in results).

At least some of the embodiments described above are summarised in the following examples E1 to E19:

E1. An apparatus (100) for determining a level of hypertension of a person, said apparatus comprising: an acquiring module (110) configured to acquire image data defining a retinal image of a retina of the person that has been captured by a retinal imaging system; a processing module (120) configured to process the image data to identify a plurality of vessel segments present in the retinal image; a determining module (130) configured to determine respective widths of vessel segments of at least a subset of the plurality of vessel segments present in the retinal image; and a calculating module (140) configured to calculate, as a vascular summary metric, at least one average value or median value of the determined widths of the vessel segments present in the retinal image, to determine a level of hypertension by which the person has been affected.

E2. The apparatus (100) of E1, wherein the calculating module (140) is further configured to calculate the vascular summary metric by categorising each of the plurality of the vessel segments as an artery or non-artery; and calculating at least one of: an average arterial width, or a median arterial width.

E3. The apparatus (100) of any of E1-E2, wherein the calculating module (140) is further configured to calculate the vascular summary metric by at least one of: calculating a ratio of the average arterial width to an average venule width, or calculating a ratio of the median arterial width to a median venule width, wherein the average venule width or median venule width is calculated using the widths of the vessel segments classified as non-artery.

E4. The apparatus (100) of any of E1-E3, wherein the calculating module (140) is further configured to calculate the vascular summary metric by selecting a reduced subset of the subset of the plurality of vessel segments for which the widths have been determined; and calculating the vascular summary metric based on the widths of the selected reduced subset of the plurality of vessel segments.

E5. The apparatus (100) of E4, wherein calculating module (140) is further configured to select the reduced subset by, in a case where each of the plurality of vessel segments has been categorised as veins or arteries, selecting, from among the vessel segments categorised as veins, a first predetermined number of widest vessel segments and selecting, from among the vessel segments categorised as arteries, a second predetermined number of widest vessel segments.

E6. The apparatus (100) of any of E1-E5, wherein the processing module is further configured to process the image data to identify the plurality of vessel segments based on a classification algorithm trained on image data defining retinal images of a plurality of subjects.

E7. The apparatus (100) of any of E1-E6, wherein the classification algorithm is based on a supervised learning algorithm.

E8. The apparatus (100) of E7, wherein the supervised learning algorithm is a neural network.

E9. The apparatus (100) of any of E1-E8, wherein the processing module is further configured to process the image data to identify a plurality of vessel segments by selecting a region of interest; and processing the image data to identify a plurality of vessel segments in the selected region of interest.

E10. The apparatus (100) of any of E1-E9, the processing module is further configured to process the image data to identify a plurality of vessel segments by processing the image data to locate retinal landmarks.

E11. The apparatus (100) of E10, wherein, in a case where the processing module is further configured to process the image data to identify a plurality of vessel segments by selecting a region of interest and processing the image data to identify a plurality of vessel segments in the selected region of interest, the region of interest is selected using the located retinal landmarks.

E12. The apparatus (100) of any of E1-E11, wherein the processing module is further configured to process the image data to identify the plurality of vessel segments by processing the image data to improve recognition of vessel segments by least one of: pre-processing the image data using at least one of an adaptive histogram equalisation technique or using a morphological image crossing technique; enhancing the image data or the pre-processed image data in order to aid detection of retinal features using Hessian filtering; creating the vessel segments by splitting a segmented vascular network; or cleaning the plurality of vessel segments by removing disconnected regions, branches, and offshoots that are unlikely to be the vessel segments.

E13. The apparatus (100) of any of E1-E12, wherein the determining module is further configured to determine the width of at least a subset of the plurality of vessel segments by shortening the vessel segments such that the vessel segments have a more uniform width.

E14. The apparatus (100) of any of E1-E13, wherein the determining module is further configured to determine the width of at least a subset of the plurality of vessel segments by measuring a width of each of the identified plurality of vessel segments in the retinal image; and converting the measured width into real units.

E15. The apparatus (100) of any of E1-E14, wherein the determining module is further configured to determine whether a retinal vasculature has been affected by hypertension by comparing the vascular summary metric to a predetermined threshold.

E16. The apparatus (100) of any of E1-E15, wherein the retinal image is captured by either of a scanning laser ophthalmoscope, SLO, or an ophthalmoscope.

E17. A computer program which, when executed by a computer, causes the computer to perform the method comprising: acquiring image data defining a retinal image of a retina of the person that has been captured by a retinal imaging system; processing the image data to identify a plurality of vessel segments present in the retinal image; determining respective widths of vessel segments of at least a subset of the plurality of vessel segments present in the retinal image; and calculating, as a vascular summary metric, at least one average value or median value of the determined widths of the vessel segments present in the retinal image, to determine a level of hypertension by which the person has been affected.

E18. A non-transitory computer-readable storage medium storing the computer program according to E17.

E19. A signal carrying the computer program according to E17.

At least some example aspects described herein avoid limitations, specifically rooted in computer technology, relating to conventional computerized and automated methods for detecting or predicting hypertension based on retinal images, such as the Knudtson method. Conventional methods, such as the Knudtson method, tend to lack accuracy and/or precision in the use of retinal images to detect or predict hypertension due to a reliance on a relationship between a level of hypertension and the diameter of the hidden CRV, which is not visible in retinal images. Instead of relying on such a relationship between a level of hypertension and a diameter of the CRV (or values for CRAE or CRVE), like conventional methods, at least some example aspects herein instead can predict hypertension using retinal images by relying on a direct relationship between measurements of a retinal vasculature visible in a retinal image and a level of hypertension. Example aspects herein can determine a level of hypertension without making any estimate or assumptions about the hidden CRV, branching coefficients, vessel equivalents or the like. Accordingly, possible variations introduced by estimation can be avoided. At least some example aspects herein also can detect and/or predict hypertension with greater accuracy than conventional methods. As such, example aspects described herein improve methodology for (early) detection of hypertension from retinal images, as well as for (early) determination of levels of hypertension from retinal images, and improve the field(s) of medical imaging, medical devices, hypertension detection, and related clinical protocols.

Also, by virtue of the capabilities of at least some example aspects described herein, which are rooted in computer technology, those example aspects described herein also improve computer technology by, for example and without limitation, avoiding processing and memory requirements required to estimate or determine assumptions about the hidden CRV, branching coefficients, vessel equivalents or the like, and also by providing more accurate and faster determinations regarding hypertension detection and/or prediction than those achieved by conventional methods, such as the Knudtson method.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device or medium, may be used to program a computer system or other electronic device. The machine- or computer-readable device/medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration.

They may find applicability in any computing or processing environment. The terms "computer-readable", "machine-accessible medium", "machine-readable medium", "instruction store", "computer-readable storage medium", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limitations on the scope of any inventions or of what may be claimed, but rather as descriptions of features specific to particular embodiments described herein.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A non-transitory, computer-readable storage medium storing computer program instructions which, when executed by a computer, cause the computer to execute a method for determining a level of hypertension of a person, said method comprising:
    acquiring image data defining a retinal image of a retina of the person that has been captured by a retinal imaging system;
    processing the image data based on a classification algorithm, which has been trained on image data defining retinal images of a plurality of subjects, to identify a plurality of vessel segments present in the retinal image, wherein the processing comprises:
        demarcating a region of interest, which is confined to a portion of the retinal image showing a near periphery of the retina that comprises an annular segment subtending 180 degrees nasal to the optic disc, from a remainder of the retinal image; and
        processing the image data to identify the plurality of vessel segments in the region of interest of the retinal image;
    determining respective widths of vessel segments of at least a subset of the plurality of vessel segments present in the region of interest of the retinal image;
    calculating, as at least one value of a vascular summary metric, at least one of an average value of and a median value of the determined widths of the vessel segments present in the region of interest of the retinal image; and
    using the at least one value of the vascular summary metric and a relationship between the vascular summary metric and a level of hypertension to determine a level of hypertension by which the person has been affected.

2. The non-transitory, computer-readable storage medium of claim 1, wherein calculating as at least one value of the vascular summary metric comprises:

categorizing each of the plurality of the vessel segments as at least one of an artery and a non-artery; and
calculating at least one of:
an average arterial width, and
a median arterial width.

3. The non-transitory, computer-readable storage medium of claim 2, wherein calculating as at least one value of the vascular summary metric further comprises at least one of:
calculating a ratio of the average arterial width to an average venule width calculated using the widths of the vessel segments classified as non-artery; and
calculating a ratio of the median arterial width to a median venule width calculated using the widths of the vessel segments classified as non-artery.

4. The non-transitory, computer-readable storage medium of claim 1, wherein calculating as at least one value of the vascular summary metric comprises:
selecting a reduced subset of the subset of the plurality of vessel segments for which the widths have been determined; and
calculating the at least one value of the vascular summary metric based on the widths of the selected reduced subset of the plurality of vessel segments.

5. The non-transitory, computer-readable storage medium of claim 4, wherein selecting the reduced subset comprises, in a case where each of the plurality of vessel segments has been categorized as at least one of veins and arteries, selecting, from among the vessel segments categorized as veins, a first predetermined number of widest vessel segments and selecting, from among the vessel segments categorized as arteries, a second predetermined number of widest vessel segments.

6. The non-transitory, computer-readable storage medium of claim 1, wherein the region of interest is an annulus sector of the retinal image, apart from the optic disc in the retinal image, showing a near periphery of the retina nasal to the optic disc.

7. The non-transitory, computer-readable storage medium of claim 1, wherein:
processing the image data to identify a plurality of vessel segments further comprises processing the image data to locate retinal landmarks;
and the region of interest is demarcated using the located retinal landmarks.

8. The non-transitory, computer-readable storage medium of claim 1, wherein processing the image data to identify the plurality of vessel segments comprises processing the image data to improve recognition of vessel segments by at least one of:
pre-processing the image data using at least one of an adaptive histogram equalization technique and a morphological image crossing technique;
enhancing at least one of the image data and pre-processed image data in order to aid detection of retinal features using Hessian filtering;
creating the vessel segments by splitting a segmented vascular network; and
cleaning the plurality of vessel segments by removing disconnected regions, branches, and offshoots that are unlikely to be the vessel segments.

9. The non-transitory, computer-readable storage medium of claim 1, wherein determining the respective widths of the vessel segments of at least a subset of the plurality of vessel segments comprises shortening the vessel segments such that the vessel segments have a more uniform width.

10. The non-transitory, computer-readable storage medium of claim 1, wherein determining the respective widths of the vessel segments of at least a subset of the plurality of vessel segments comprises:
measuring a width of each of the vessel segments of the at least a subset of the plurality of vessel segments; and
converting each measured width into metric units.

11. The non-transitory, computer-readable storage medium of claim 1, wherein determining a level of hypertension by which the person has been affected includes determining whether a retinal vasculature has been affected by hypertension by comparing the at least one value of the vascular summary metric to a predetermined threshold.

12. An apparatus for determining a level of hypertension of a person, said apparatus comprising:
an acquiring module configured to acquire image data defining a retinal image of a retina of the person that has been captured by a retinal imaging system;
a processing module configured to process the image data based on a classification algorithm, which has been trained on image data defining retinal images of a plurality of subjects, to identify a plurality of vessel segments present in the retinal image, by:
demarcating a region of interest, which is confined to a portion of the retinal image showing a near periphery of the retina that comprises an annular segment subtending 180 degrees nasal to the optic disc, from a remainder of the retinal image; and
processing the image data to identify the plurality of vessel segments in the region of interest of the retinal image;
a determining module configured to determine respective widths of vessel segments of at least a subset of the plurality of vessel segments present in the region of interest of the retinal image; and
a calculating module configured to calculate, as at least one value of a vascular summary metric, at least one of an average value of and a median value of the determined widths of the vessel segments present in the region of interest of the retinal image, and to use the at least one value of the vascular summary metric and a relationship between the vascular summary metric and a level of hypertension to determine a level of hypertension by which the person has been affected.

13. The apparatus of claim 12, wherein the calculating module is further configured to calculate the at least one value of the vascular summary metric by categorizing each of the plurality of the vessel segments as at least one of an artery and a non-artery; and calculating at least one of: an average arterial width, and a median arterial width.

14. The apparatus of claim 12, wherein the calculating module is further configured to calculate the at least one value of the vascular summary metric by at least one of:
calculating a ratio of the average arterial width to an average venule width calculated using the widths of the vessel segments classified as non-artery, and
calculating a ratio of the median arterial width to a median venule width calculated using the widths of the vessel segments classified as non-artery.

15. The apparatus of claim 12, wherein the calculating module is further configured to calculate the at least one value of the vascular summary metric by selecting a reduced subset of the subset of the plurality of vessel segments for which the widths have been determined; and calculating the at least one value of the vascular summary metric based on the widths of the selected reduced subset of the plurality of vessel segments.

16. The apparatus of claim 15, wherein the calculating module is further configured to select the reduced subset by, in a case where each of the plurality of vessel segments has been categorized as at least one of veins and arteries, selecting, from among the vessel segments categorized as veins, a first predetermined number of widest vessel segments and selecting, from among the vessel segments categorized as arteries, a second predetermined number of widest vessel segments.

17. The apparatus of claim 12, wherein the processing module is further configured to process the image data to identify the plurality of vessel segments based on a classification algorithm trained on image data defining retinal images of a plurality of subjects.

18. The apparatus of claim 12, wherein the classification algorithm comprises a neural network trained on the image data to generate a set of parameters for the neural network.

19. A non-transitory, computer-readable storage medium storing computer program instructions which, when executed by a computer, cause the computer to execute a method for determining a level of hypertension of a person, said method comprising:
   acquiring image data defining a retinal image of a retina of the person that has been captured by a retinal imaging system;
   processing the image data based on a classification algorithm, which has been trained on image data defining retinal images of a plurality of subjects, to identify a plurality of vessel segments present in the retinal image, wherein the processing comprises:
      demarcating a region of interest, which is confined to a portion of the retinal image showing a near periphery of the retina that comprises a half-concentric region nasal to the optic disc, from a remainder of the retinal image; and
      processing the image data to identify the plurality of vessel segments in the region of interest of the retinal image;
   determining respective widths of vessel segments of at least a subset of the plurality of vessel segments present in the region of interest of the retinal image;
   calculating, as at least one value of a vascular summary metric, at least one of an average value of and a median value of the determined widths of the vessel segments present in the region of interest of the retinal image; and
   using the at least one value of the vascular summary metric and a relationship between the vascular summary metric and a level of hypertension to determine a level of hypertension by which the person has been affected.

20. An apparatus for determining a level of hypertension of a person, said apparatus comprising:
   an acquiring module configured to acquire image data defining a retinal image of a retina of the person that has been captured by a retinal imaging system;
   a processing module configured to process the image data based on a classification algorithm, which has been trained on image data defining retinal images of a plurality of subjects, to identify a plurality of vessel segments present in the retinal image, by:
      demarcating a region of interest, which is confined to a portion of the retinal image showing a near periphery of the retina that comprises a half-concentric region nasal to the optic disc, from a remainder of the retinal image; and
      processing the image data to identify the plurality of vessel segments in the region of interest of the retinal image;
   a determining module configured to determine respective widths of vessel segments of at least a subset of the plurality of vessel segments present in the region of interest of the retinal image; and
   a calculating module configured to calculate, as at least one value of a vascular summary metric, at least one of an average value of and a median value of the determined widths of the vessel segments present in the region of interest of the retinal image, and to use the at least one value of the vascular summary metric and a relationship between the vascular summary metric and a level of hypertension to determine a level of hypertension by which the person has been affected.

* * * * *